United States Patent [19]

Pickart

[11] Patent Number: 5,118,665
[45] Date of Patent: Jun. 2, 1992

[54] ANTI-OXIDATIVE AND ANTI-INFLAMMATORY METAL:PEPTIDE COMPLEXES AND USES THEREOF

[75] Inventor: Loren R. Pickart, Bellevue, County of King, Wash.

[73] Assignee: ProCyte Corporation, Redmond, Wash.

[21] Appl. No.: 478,091

[22] Filed: Feb. 9, 1990

[51] Int. Cl.$^5$ .......................... C07K 5/08; C07K 9/00
[52] U.S. Cl. .......................................... 514/6; 514/8; 514/17; 514/18; 530/322; 530/329; 530/330; 530/331
[58] Field of Search .............. 530/322, 329, 330, 331; 514/8, 17, 18, 6

[56] References Cited

U.S. PATENT DOCUMENTS

| | | | |
|---|---|---|---|
| 3,194,732 | 7/1965 | Neuhauser | 167/58 |
| 3,551,554 | 12/1970 | Herschler | 424/7 |
| 3,558,770 | 1/1971 | Gordon et al. | 424/80 |
| 3,758,682 | 9/1973 | Huber et al. | 424/177 |
| 3,767,784 | 10/1973 | Gluck | 424/28 |
| 3,832,338 | 8/1974 | Huber et al. | 260/113 |
| 4,022,888 | 5/1977 | Huber et al. | 424/177 |
| 4,167,945 | 9/1979 | Gottlieb | 128/334 R |
| 4,177,261 | 12/1979 | Dietze et al. | 424/101 |
| 4,263,428 | 4/1981 | Apple et al. | 536/17 A |
| 4,287,184 | 9/1981 | Young | 424/177 |
| 4,440,788 | 4/1984 | Terayama et al. | 424/320 |
| 4,665,054 | 5/1987 | Pickart | 514/6 |
| 4,760,051 | 7/1988 | Pickart | 514/6 |
| 4,767,753 | 8/1988 | Pickart | 514/18 |

FOREIGN PATENT DOCUMENTS

| | | |
|---|---|---|
| 0078228 | 4/1982 | European Pat. Off. |
| 86/00222 | 1/1986 | PCT Int'l Appl. |
| 88/08695 | 11/1988 | PCT Int'l Appl. |
| 88/08715 | 11/1988 | PCT Int'l Appl. |

OTHER PUBLICATIONS

Pickart et al., "Growth-Modulating Tripeptide (glycylhistidyllysine): Association with Copper and Iron in Plasma and Stimulation of Adhesive and Growth of Hepatoma Cells in Culture by Tripeptide-Metal Ion Complexes," *J. Physiol.* 102(2):129–139, 1980.
Williams et al., "Glycyl-L-Histidyl-L-Lysine, a Growth Promoting Factor for Human Cells," *Cytobios* 27(105):19–25, 1980.
Mochida Pharmaceutical Co., Ltd., "Anti-Inflammatory Injections Containing Superoxide Dismutase," Jpn. Kokai Tokkyo Koho, 81 07,720,27 Jan. 1981 (cited in *Chem. Abstracts* 94:145386f, 1981).
Kwa, "Glycyl-L-Histidyl-L-Lysine: Synthesis of Analogs and NMR Studies," Ph.D. Thesis, University of Washington, 1983.
Loker, "Synthesis of Blood Serum Peptide Cell Growth Factors," Ph.D. Thesis, University of Washington, 1980.
Pickart, "The Biological Effects and Mechanism of Action of the Plasma Tripeptide Glycyl-L-Histidyl-L-Lysine," *Lymphonkines* 8:425–446, 1983.
Poole et al., "Stimulation of Rat Peritoneal Mast Cell Migration by Tumor-Derived Peptides," *Cancer Research* 43:5857–5861, 1983.
Raju et al., "Ceruloplasmin, Copper Ions, and Angiogenesis," *JNCI* 69(5):1183–1188, 1982.
Freedman et al., "Structure of the Glycyl-L-Histidyl-L-Lysine-Copper(II) Complex in Solution," *Biochemistry* 21:4540–4544, 1982.
Kwa et al., "PMR Studies of Cu(II) and Zn(II) Interaction with Glycyl-L-Histidyl-L-Lysine and Related Peptides," *Peptides: Structure and Function* 8:805–808, 1983.
Perkins et al., "The Structure of a Copper Complex of the Growth Factor Glycyl-L-Histidyl-L-Lysine at 1.1 Å Resolution," *Inorganica Chimica Acta* 82:93–99, 1984.
Kimoto et al., "Enhancement of Antitumor Activity of Ascorbate Against Ehrich Ascites Tumor Cells by the Copper: Glycylglycylhistidine Complex," *Cancer Research* 43:824–828, 1983.
Sorenson, "Copper Complexes: A Physiologic Approach to Treatment of Chronic Diseases," *Comprehensive Therapy* 11(4):49–64, 1985.
Pickart et al., "Inhibition of the Growth of Cultured Cells and an Implanted Fibrosarcoma by Aroylhydrazone Analogs of the Gly-His-Lys-Cu(II) Complex," *Biochem. Pharmacol.* 32(24):3868–3871, 1983.
Pickart et al., "Growth-Modulating Plasma Tripeptide May Function by Facilitating Copper Uptake Into Cells," *Nature* 288:715–717, 1980.
"Newsreport on Use of GGH-Cu(II) and Ascorbic Acid," *Natural Healing Annual* 1986, p. 38 (M. Bricklin (ed.), Prevention Magazine, Rodale Press, Emmaus, Pa.).
Pickart et al., "A Synthetic Tripeptide which Increases Survival of Normal Liver Cells, and Stimulates Growth in Hepatoma Cells," *Biochem. Biophys. Res. Commun.* 54(2):562–66, 1973.
Aonuma et al., "Studies on Anti-Ulcerogenic Protein in Inflamed Rabbit Skin Tissues," *Yakugaku Zasshi* 104(4):362–73, 1984.
Downey et al., "Acceleration of Wound Healing Using GHL-Cu(II)," *Surgical Forum* 36:573–75, 1985.
Pickart et al., "A Human Plasma Growth Factor with Superoxide Dismutase-like and Wound-healing Properities," Superoxide Dim. Chem., Biol. Med. Proc. Int. Conf. 4th 1985 (Pub. 1986), 555–57. (cited in *Chem Abstract* 106:13579c).
Frater-Schroder et al., "Tumor Necrosis Factor Type α, a Potential Inhibitor of Endothelia Cell growth in vitro is Angiogenic in vivo," *Proc. Natl. Acad. Sci. USA* 34:5277–81 (1987).
Pickart, "The use of Glycylhistidyllysine in Culture Systems," *In Vitro* 17(6):459–466 (1981).

*Primary Examiner*—Lester L. Lee
*Attorney, Agent, or Firm*—Seed and Berry

[57] ABSTRACT

Compositions and methods for enhancing or restoring the resistance of a warm blooded animal to oxidative or inflammatory damage caused be release of reactive oxygen species by certain immune cells and other physiological processes are disclosed. The compositions include metal:peptide and metal:peptide:chelating agent complexes.

40 Claims, No Drawings

ANTI-OXIDATIVE AND ANTI-INFLAMMATORY METAL:PEPTIDE COMPLEXES AND USES THEREOF

TECHNICAL FIELD

The present invention relates generally to metal:peptide complexes and uses thereof, and more particularly, to metal:peptide complexes which possess anti-oxidative and anti-inflammatory activity.

BACKGROUND OF THE INVENTION

Highly reactive oxygen species such as superoxide anion ($O_2^-$), hydrogen peroxide ($H_2O_2$), hydroxyl radical (.OH), and lipid peroxides (LOOH) are involved in a number of human diseases. For example, oxygen radicals have been implicated in autoimmune diseases, arthritis, tissue damage caused by environmental pollutants, cigarette smoke and drugs, tissue injury during surgery and transplantation, as well as a variety of other conditions (Halliwell, B., *Fed. Amer. Soc. Exp. Biol.* 1:358–364, 1987).

Reactive oxygen species are also generated during the response to injury by phagocytic cells. One of the early events in the wound healing response is the cleansing and sterilization of the wound by neutrophils and macrophages. A mechanism for this sterilization is the generation of the highly reactive superoxide anion and hydrogen peroxide. Superoxide anion and hydrogen peroxide will, in the presence of iron or other redox active transition metal complexes, generate hydroxyl radical. The hydroxyl radical is a potent oxidant which will initiate the free radical oxidation of fatty acids and the oxidative degradation of other biomolecules.

One of the most vital areas in which reactive oxygen species cause tissue damage is in post-injury damage to the brain and spinal chord, and in reperfusion injury to ischemic tissue following surgery and transplantation (e.g., the heart). A sudden inrush of oxygenated blood and activated phagocytic cells leads to superoxide anion and hydrogen peroxide formation. These species do direct damage to the tissue and also react with iron, as discussed above, to generate the very reactive hydroxyl radical.

Iron has also been shown to have a direct role in the initiation of lipid peroxidation. An Fe(II)/Fe(III) complex can serve as an initiator of lipid oxidation. In addition, many iron complexes can catalyze the decomposition of lipid hydroperoxides to the corresponding lipid alkoxy radicals, which will continue the peroxidation cascade. The major storage site for iron in serum and tissue is ferritin. This ubiquitous storage protein (M.W. ~450,000) can store up to 4500 atoms of iron per protein molecule. It has been shown that superoxide anion can promote the mobilization of iron from ferritin. This free iron may then catalyze lipid peroxidation and the conversion of superoxide anion to the more damaging hydroxyl radical.

A mechanism for the generation of the hydroxyl radical is illustrated below:

Neutrophils, Reperfusion Injury

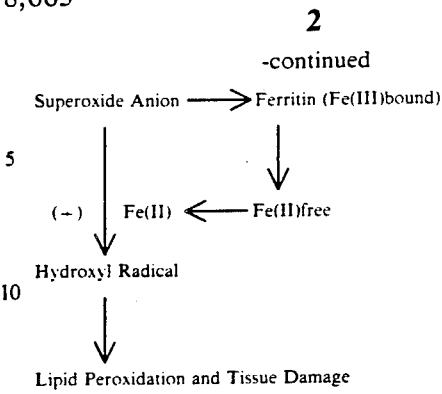

Lipid Peroxidation and Tissue Damage

A number of therapeutic agents have been utilized to prevent or limit oxidative damage. For example, agents such as superoxide dismutase (a 32,000 Dalton molecular weight enzyme), anti-oxidants (such as Vitamin E and C), and transition metal chelators have been shown to eliminate these ions and prevent them from participating in free radical reactions. Additional compounds which possess anti-oxidative properties include glycyl-L-histidyl-L-lysine:copper(II) and certain derivatives thereof, U.S. Pat. Nos. 4,760,051, 4,665,054 and 4,877,770, each of which are incorporated herein by reference.

As mentioned above, due to the severity and incidence of disease states in which reactive oxygen species play a role, there is a need in the art for effective anti-oxidant agents. Desirably, such agents should eliminate reactive oxygen species, inhibit the mobilization of metal ions such as iron which may participate in the generation of such species, and be available at the site of injury or reactive species generation.

SUMMARY OF THE INVENTION

Briefly stated, the present invention discloses metal:-peptide complexes which possess anti-oxidative and anti-inflammatory activity. These complexes can be used in pharmaceutical preparations to inhibit oxidative and inflammatory processes which can lead to tissue damage.

The metal:peptide complexes of the present invention include compounds of the following general formulas designated A through I:

A:[glycyl-L-histidyl-L-lysine-R]:metal wherein
R is an aminoalkyl moiety containing from 1 to 18 carbon atoms, or is L-tryptophan, (glycyl)$_y$-L-tryptophan, where y=1–4, L-prolyl-$X_1$-L-phenylalanyl-$X_2$ or $X_1$-L-phenylalanyl-$X_2$, where $X_1$ and $X_2$ are selected from the group consisting of L-valine, L-alanine and glycine, and where $X_1$ and $X_2$ are not both L-valine, ($X_3$)$_n$-L-tryptophan, where $X_3$ is a —$CH_2$— or —CH(OH)— moiety and n=4–20, or -($X_4$)$_n$, where $X_4$ is a naturally occurring carbohydrate such as glucose, mannose, galactose, glucosamine or galactosamine and n=1–5; and
metal is copper(II) or manganese(II);

B:[glycyl-$R_1$-$R_2$-$R_3$]:metal wherein
$R_1$ is selected from the group consisting of L-histidyl, L-(3-W)-histidyl and L-(5-W)-histidyl, where W is an alkyl moiety containing from 1 to 12 carbons atoms or aryl moiety containing from 6-12 carbon atoms;

$R_2$ is -NHCH$((CH_2)_n$NH$_3^+)$CO- where n=5-10;

$R_3$ is —NH$_2$, an aminoalkyl moiety containing from 1 to 18 carbon atoms, or is L-tryptophan, (glycyl)$_y$-L-tryptophan, where y=1-4, L-prolyl-$X_1$-L-phenylalanyl-$X_2$ or $X_1$-L-phenylalanyl-$X_2$, where $X_1$ and $X_2$ are selected from the group consisting of L-valine, L-alanine and glycine, and where $X_1$ and $X_2$ are not both L-valine, $(X_3)_n$-L-tryptophan, where $X_3$ is a —CH$_2$— or —CH(OH)— moiety and n=4-20, or -$(X_4)_n$, where $X_4$ is a naturally occurring carbohydrate such as glucose, mannose, galactose, glucosamine or galactosamine and n=1-5; and metal is copper(II) or manganese(II);

C:[glycyl-$R_1$-$R_2$-$R_3$]:metal wherein $R_1$ is selected from the group consisting of L-(3-W')-histidyl and L-(5-W')-histidyl where W' is an alkyl moiety containing from 1 to 12 carbons atoms or aryl moiety containing from 6-12 carbon atoms;

$R_2$ is L-lysyl;

$R_3$ is -NH$_2$, an aminoalkyl moiety containing from 1 to 18 carbon atoms, or is L-tryptophan, (glycyl)$_y$-L-tryptophan, where y=1-4, L-prolyl-$X_1$-L-phenylalanyl-$X_2$ or $X_1$-L-phenylalanyl-$X_2$, where $X_1$ and $X_2$ are selected from the group consisting of L-valine, L-alanine and glycine, and where $X_1$ and $X_2$ are not both L-valine, $(X_3)_n$-L-tryptophan, where $X_3$ is a —CH$_2$— or —CH(OH)— moiety and n=4-20, or -$(X_4)_n$, where $X_4$ is a naturally occurring carbohydrate such as glucose, mannose, galactose, glucosamine or galactosamine and n=1-5; and metal is copper(II) or manganese(II);

D:[glycyl-$R_1$-$R_2$-$R_3$]:metal wherein $R_1$ is selected from the group consisting of L-histidyl, L-(3-W')-histidyl and L-(5-W')-histidyl where W' is an alkyl moiety containing from 1 to 12 carbons atoms or aryl moiety containing from 6-12 carbon atoms;

$R_2$ is a basic amino acid such as arginine, a basic amino moiety such as cadaverine, spermine or spermidine, or a modified basic amino acid such as caprolactone;

$R_3$ is hydrogen, —NH$_2$, an alkyl moiety containing from 1 to 18 carbon atoms, an aryl moiety containing from 6 to 12 carbon atoms, an alkoxy moiety containing from 1 to 18 carbon atoms, an aryloxy moiety containing from 6-12 carbon atoms, an aminoalkyl moiety containing from 1 to 18 carbon atoms, or is L-tryptophan, (glycyl)$_y$-L-tryptophan, where y=1-4, L-prolyl-$X_1$-L-phenylalanyl-$X_2$ or $X_1$-L-phenylalanyl-$X_2$, where $X_1$ and $X_2$ are selected from the group consisting of L-valine, L-alanine and glycine, $(X_3)_n$-L-tryptophan, where $X_3$ is a —CH$_2$— or —CH(OH)— moiety and n=4-20, or -$(X_4)_n$, where $X_4$ is a naturally occurring carbohydrate such as glucose, mannose, galactose, glucosamine or galactosamine and n=1-5; and metal is copper(II) or manganese(II);

E:[$R_1$-$R_2$-glycine-$R_3$]:metal wherein $R_1$ is L-lysyl or —NHCH$((CH_2)_n$NH$_3^+)$CO— where n=5-10;

$R_2$ is selected from the group consisting of L-histidyl, L-(3-W')-histidyl and L-(5-W')-histidyl where W' is an alkyl moiety containing from 1 to 12 carbons atoms or aryl moiety containing from 6-12 carbon atoms;

$R_3$ is hydrogen, —NH$_2$, an alkyl moiety containing from 1 to 18 carbon atoms, an aryl moiety containing from 6 to 12 carbon atoms, an alkoxy moiety containing from 1 to 18 carbon atoms, an aryloxy moiety containing from 6-12 carbon atoms, an aminoalkyl moiety containing from 1 to 18 carbon atoms, or is L-tryptophan, (glycyl)$_y$-L-tryptophan, where y=1-4, L-prolyl-$X_1$-L-phenylalanyl-$X_2$ or $X_1$-L-phenylalanyl-$X_2$, where $X_1$ and $X_2$ are selected from the group consisting of L-valine, L-alanine and glycine, $(X_3)_n$-L-tryptophan, where $X_3$ is a —CH$_2$— or —CH(OH)— moiety and n=4-20, or —$(X_4)_n$, where $X_4$ is a naturally occurring carbohydrate such as glucose, mannose, galactose, glucosamine or galactosamine and n=1-5; and metal is copper(II) or manganese(II);

F:[$R_1$-$R_2$-$R_3$-$R_4$]:metal wherein $R_1$ is L-lysyl or —NHCH$((CH_2)_n$NH$_3^+)$CO— where n=5-10;

$R_2$ is selected from the group consisting of L-histidyl, L-(3-W')-histidyl and L-(5-W')-histidyl where W is an alkyl moiety containing from 1 to 12 carbons atoms or aryl moiety containing from 6-12 carbon atoms;

$R_3$ is a basic amino acid such as arginine, an amino moiety such as cadaverine, spermine or spermidine, or a modified basic amino acid such as caprolactone;

$R_4$ is hydrogen, —NH$_2$, and alkyl moiety containing from 1 to 18 carbon atoms, an aryl moiety containing from 6 to 12 carbon atoms, an alkoxy moiety containing from 1 to 18 carbon atoms, an aryloxy moiety containing from 6-12 carbon atoms, an aminoalkyl moiety containing from 1 to 18 carbon atoms, or is L-tryptophan, (glycyl)$_y$-L-tryptophan, where y=1-4, L-prolyl-$X_1$-L-phenylalanyl-$X_2$ or $X_1$-L-phenylalanyl-$X_2$, where $X_1$ and $X_2$ are selected from the group consisting of L-valine, L-alanine and glycine, $(X_3)_n$-L-tryptophan, where $X_3$ is a —CH$_2$— or —CH(OH)— moiety and n=4-20, or -$(X_4)_n$, where $X_4$ is a naturally occurring carbohydrate such as glucose, mannose, galactose, glucosamine or galactosamine and n=1-5; and metal is copper(II) or manganese(II);

G:[$R_1$-glycyl-$R_2$-$R_3$]:metal wherein $R_1$ is selected from the group consisting of L-histidyl, L-(3-W)-histidyl and L-(5-W)-histidyl where W is an alkyl moiety containing from 1 to 12 carbons atoms or aryl moiety containing from 6-12 carbon atoms;

$R_2$ is L-lysyl, —NHCH$((CH_2)_n$NH$_3^+)$CO—, where n=5-10, or a basic amino acid such as arginine, an amino moiety such as cadaverine, spermine or spermidine, or a modified basic amino acid such as caprolactone;

$R_3$ is hydrogen, $-NH_2$, an alkyl moiety containing from 1 to 18 carbon atoms, an aryl moeity containing from 6 to 12 carbon atoms, an alkoxy moiety containing from 1 to 18 carbon atoms, an aryloxy moiety containing from 6-12 carbon atoms, an aminoalkyl moeity containing from 1 to 18 carbon atoms, or is L-tryptophan, (glycyl)$_y$-L-tryptophan, where $y=1-4$, L-prolyl-$X_1$-L-phenylalanyl-$X_2$ or $X_1$-L-phenylalanyl-$X_2$, where $X_1$ and $X_2$ are selected from the group consisting of L-valine, L-alanine and glycine, $(X_3)_n$-L-tryptophan, where $X_3$ is a $-CH_2-$ or $-CH(OH)-$ moiety and $n=4-20$, or $-(X_4)_n$, where $X_4$ is a naturally occurring carbohydrate such as glucose, mannose, galactose, glucosamine or galactosamine and $n=1-5$; and metal is copper(II) or manganese(II);

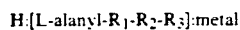

wherein $R_1$ is selected from the group consisting of L-histidyl, L-(3-W')-histidyl and L-(5-W')-histidyl where W' is an alkyl moiety containing from 1 to 12 carbons atoms or aryl moiety containing from 6-12 carbon atoms;

$R_2$ is L-lysyl or $-NHCH((CH_2)_nNH_3^+)CO-$ where $n=5-10$;

$R_3$ is $-NH_2$, an aminoalkyl moiety containing from 1 to 18 carbon atoms, or is L-tryptophan, (glycyl)$_y$-L-tryptophan, where $y=1-4$, L-prolyl-$X_1$-L-phenylalanyl-$X_2$ or $X_1$-L-phenylalanyl-$X_2$, where $X_1$ and $X_2$ are selected from the group consisting of L-valine, L-alanine and glycine, and where $X_1$ and $X_2$ are not both L-valine, $(X_3)_n$-L-tryptophan, where $X_3$ is a $-CH_2-$ or $-CH(OH)-$ moiety and $n=4-20$, or $-(X_4)_n$, where $X_4$ is a naturally occurring carbohydrate such as glucose, mannose, galactose, glucosamine or galactosamine and $n=1-5$; and metal is copper(II) or manganese(II); and

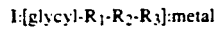

wherein $R_1$ is L-lysyl or $-NHCH((CH_2)_nNH_3^+)CO-$ where $n=5-10$ $R_2$ is selected from the group consisting of L-histidyl, L-(3-W)-histidyl and L-(5-W)-histidyl where W is an alkyl moiety containing from 1 to 12 carbons atoms or aryl moiety containing from 6-12 carbon atoms;

$R_3$ is hydrogen, $-NH_2$, an alkyl moiety containing from 1 to 18 carbon atoms, an aryl moiety containing from 6 to 12 carbon atoms, an alkoxy moiety containing from 1 to 18 carbon atoms, an aryloxy moiety containing from 6-12 carbon atoms, an aminoalkyl moiety containing from 1 to 18 carbon atoms, or is L-tryptophan, (glycyl)$_y$-L-tryptophan, where $y=1-4$, L-prolyl-$X_1$-L-phenylalanyl-$X_2$ or $X_1$-L-phenylalanyl-$X_2$, where $X_1$ and $X_2$ are selected from the group consisting of L-valine, L-alanine and glycine, $(X_3)_n$-L-tryptophan, where $X_3$ is a $-CH_2-$ or $-CH(OH)-$ moiety and $n=4-20$, or $-(X_4)_n$, where $X_4$ is a naturally occurring carbohydrate such as glucose, mannose, galactose, glucosamine or galactosamine and $n=1-5$; and metal is copper(II) or manganese(II).

In another embodiment of the present invention, a chelating agent may be added to the metal:peptide complex to form a ternary metal:peptide:chelating agent complex. Suitable chelating agents include imidazole and imidazole containing compounds, such as histidine, and sulfur-containing amino acids, such as cysteine and methionine.

The present invention also discloses methods for enhancing or restoring the resistance of a warm blooded animal to oxidative or inflammatory damage caused by release of reactive oxygen species by certain immune cells and other physiological processes. The methods comprise administering to the animal a therapeutically effective amount of a metal:peptide complex of the present invention. In addition to the methods disclosed above, the complexes of the present invention may also be used for enhancing the wound healing process in animals.

Other aspects of the present invention will become evident upon reference to the following detailed description.

BEST MODE FOR CARRYING OUT THE INVENTION

The present invention discloses metal:peptide complexes which possess anti-oxidative and anti-inflammatory activity. These complexes find use in the enhancement and/or restoration of the defense of warm-blooded animals to oxidative and inflammatory damage caused by highly reactive oxygen species, and may be used in pharmaceutical preparations to inhibit oxidative and inflammatory processes which can lead to tissue damage.

The metal:peptide complexes of the present invention possess one or more of the following features for preventing oxidative damage to tissue, including:

1) Superoxide dismutase mimetic activity to remove reactive superoxide anion;

2) Inhibition of iron release from tissue storage sites to prevent formation of reactive hydroxyl radical;

3) Structural moieties to enhance lipid solubility of the compounds to increase availability at the site of lipid peroxidation reactions; and 4) Structural moieties to enhance binding to serum proteins and increase residence time of the compound at the site of injury.

The metal:peptide complexes of the present invention include compounds of the general formulas designated A through I above. For example, in Formula F if $R_1$ is L-lysyl, $R_2$ is L-histidyl, $R_3$ is arginine, $R_4$ is an n-octyl alkoxy moiety, and the metal is copper(II), the structure of the metal:peptide complex would be as follows:

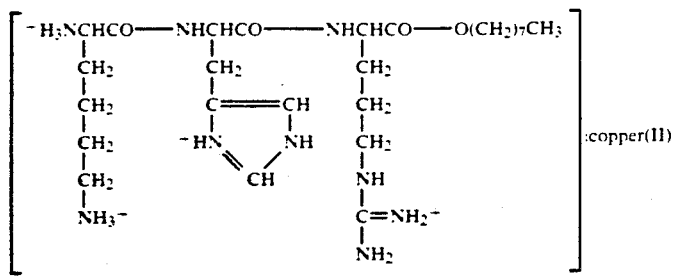

Similarly, if $R_4$ were an aminoalkyl moiety containing three carbon atoms of the formula $-NH(CH_2)_2CH_3$, the metal:peptide complex would have the following structure:

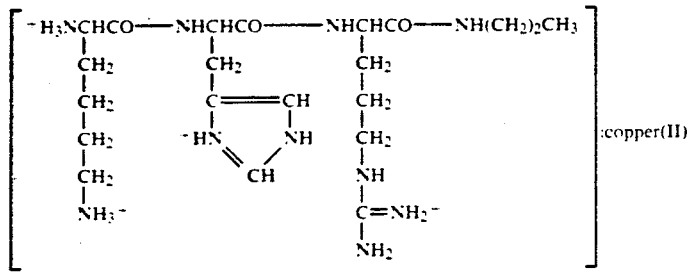

The chiral amino acids of the present invention have all been designated as the L form. However, one skilled in the art would readily appreciate that the D forms of the amino acids may be utilized as a substitute for the L forms.

The peptides of the present invention may be synthesized either by solution chemical techniques or by solid phase techniques. The general procedure involves the stepwise addition of protected amino acids to build up the desired peptide sequence. Such methodology is well known to those skilled in the art. Illustrative syntheses of complexes of the present invention are presented in the examples hereinbelow.

Within the present invention, one may utilize a molar ratio of peptide to metal of, for example, 1:1, 2:1 or greater (e.g., 3:1). Preferably, the peptide to metal molar ratio is 2:1. A significant molar excess of peptide to metal results in unbound (i.e., non-chelated) peptide. Such unbound peptide does not serve to restore or enhance the anti-oxidative or anti-inflammatory process. Moreover, metal in molar excess of the peptide is loosely bound and may inhibit rather than enhance or restore the anti-oxidative or anti-inflammatory process.

In another embodiment of the present invention, a chelating agent may be added to the metal:peptide complex to form a ternary metal:peptide:chelating agent complex. Suitable chelating agents include imidazole or imidazole-containing compounds, such as histidine, and sulfur containing amino acids, such as cysteine or methionine. Thus, if the metal:peptide complex is glycyl-L-histidyl-L-lysine:copper(II), histidine may be added to yield the ternary complex glycyl-L-histidyl-L-lysine:-copper(II):histidine. However, to form such a ternary complex, the molar ratio of metal to peptide to chelating agent must be considered. For example, if the ratio of peptide to metal is 2:1, the addition of a chelating agent to the metal:peptide complex, although possible, is difficult due to site occupancy by the peptide. However, by maintaining the ratio of peptide to metal near 1:1, a chelating group may readily be added to form the ternary complex. Preferably, the peptide to metal to chelating agent ratio is 1:1:1.

Pharmaceutical preparations of the present invention may contain the metal:peptide complex in combination with inert ingredients for topical application (i.e., pharmaceutical acceptable diluents), or contain suitable inert ingredients for either oral or parenteral applications (i.e., pharmaceutically acceptable carriers). The diluent or carrier should not interact with the metal:peptide complex to significantly reduce the effectiveness thereof. An effective dosage of pharmaceutical preparations of the present invention delivers approximately 0.01 to 10 mg of metal:peptide complex per kg body weight.

Methods for encapsulating compositions (such as in a coating of hard gelatin) for oral administration are well known in the art (Baker, Richard, *Controlled Release of Biological Active Agents*, John Wiley and Sons, 1986, incorporated herein by reference). Suitable pharmaceutically acceptable carriers for parenteral application, such as intravenous, subcutaneous or intramuscular injection, include sterile water, physiological saline, bacteriostatic saline (saline containing 0.9 mg/ml benzyl alcohol) and phosphate-buffered saline.

Pharmaceutical preparations of the present invention may be topically applied in the form of liquids, containing pharmaceutically acceptable diluents such as saline and sterile water, or be applied as lotions, creams or gels, containing additional ingredients to impart the desired texture, consistency, viscosity and appearance. Such additional ingredients are familiar to those skilled in the art and include emulsifying agents such as nonionic ethoxylated and nonethoxylated surfactants, fatty alcohols, fatty acids, organic or inorganic bases, preserving agents, wax esters, steroid alcohols, triglyceride esters, phospholipids such as lecithin and cephalin, polyhydric alcohol esters, fatty alcohol esters, hydrophilic lanolin derivatives, hydrophilic beeswax derivatives, hydrocarbon oils such as palm oil, coconut oil, mineral oil, cocoa butter waxes, silicon oils, pH balancers and cellulose derivatives.

Topical administration of the pharmaceutical preparation may by accomplished by applying an amount of the preparation directly to the desired area, such as a wound or an inflamed area. The required dosage will vary according to the particular condition to be treated, the severity of the condition, and the duration of the treatment.

When the pharmaceutical preparation is topically applied in the form of a lotion, cream or gel, the preparation may contain about 1% to about 20% of a penetration enchancing agent. Examples of penetration enhancing agents include dimethylsulfoxide (DMSO), urea and eucalyptol. In the case of a liquid pharmaceutical preparations to be applied topically, the concentration of penetration enhancing agent such as DMSO may comprise about 30% to about 80% of the pharmaceutical preparation.

EXAMPLES

To summarize the examples that follow, Examples 1-12 illustrate the synthesis of representative metal:peptide complexes of the present invention. Examples 13-17 illustrate the anti-oxidative activity of representative metal:peptide complexes of the present invention, and Examples 18-19 illustrate the inhibition of iron release form ferritin and the inhibition of lipid peroxidation by representative metal:peptide complexes of the present invention.

Specifically, Example 1 illustrates the preparation of metal:peptide complexes of the present invention by the addition of a metal chloride to the peptide. Example 2 illustrates the synthesis of glycl-L-histidyl-L-lysine n-octyl ester. Example 3 illustrates (a) the synthesis of glycyl-L-histidyl-L-lysine n-stearyl ester, and (b) the synthesis of glycyl-L-histidyl-L-lysine n-palmityl ester. Example 4 illustrates the synthesis of glycyl-L-histidyl-L-lysine n-octyl amide. Example 5 illustrates the synthesis of glycyl-L-histidyl-L-lysyl-L-valyl-L-phenylalanyl-L-valine. Example 6 illustrates the synthesis of L-alanyl-L-histidyl-L-lysine. Example 7 illustrates the synthesis of L-lysyl-L-histidyl-glycine. Example 8 illustrates the synthesis of L-lysyl-L-histidyl-glycine amide. Example 9 illustrates the synthesis of L-lysyl-L-histidyl-glycine n-octyl ester. Example 10 illustrates the synthesis of L-lysyl-L-histidyl-glycyl-L-valyl-L-phenylalanyl-L-valine. Example 11 illustrates the synthesis of glycyl-L-histidyl-caprolactam. Example 12 illustrates the synthesis of L-histidyl-glycyl-L-lysine.

Example 13 demonstrates the superoxide dismutase mimetic activity of representative metal:peptide complexes of the present invention containing peptides of a hydrophobic nature. Example 14 demonstrates the superoxide dismutase mimetic activity of representative metal:peptide complexes of the present invention in relation to the amino acid sequence. Example 15 demonstrates the superoxide dismutase mimetic activity of representative metal:peptide complexes of the present invention wherein the metal is copper(II) and manganese(II). Example 16 demonstrates the superoxide dismutase mimetic activity of representative metal:peptide complexes of the present invention containing additional chelating groups. Example 17 demonstrates the superoxide dismutase mimetic activity of representative metal:peptide complexes of the present invention containing albumin binding moieties.

Example 18 demonstrates the inhibition of iron release by ferritin utilizing representative metal:peptide complexes of the present invention. Example 19 demonstrates the inhibition of lipid peroxidation utilizing representative metal:peptide complexes of the present invention.

Although lysine is designated by the single letter "L" herein, for purposes of clarity, those skilled in the art will recognize that the single letter amino acid abbreviation for lysine is "K." Therefore, K may be substituted for L in the examples that follow.

SOURCE OF CHEMICALS

Chemicals and peptide intermediates utilized in the following examples may be purchased from a number of suppliers, for example: Sigma Chemical So., St. Louis, Mo.; Peninsula Laboratories, San Carlos, Calif.; Aldrich Chemical Company, Milwaukee, Wis.; Vega Biochemicals, Tucson, Ariz.; Pierce Chemical Co., Rockford, Ill.; Research Biochemicals, Cleveland, Ohio; Van Waters and Rogers, South San Francisco, Calif.; and Bachem, Inc., Torrance, Calif.

EXAMPLE 1

Preparation of Metal:Peptide Complexes

The metal:peptide complexes of the present invention may be synthesized by dissolving the peptide in distilled water, followed by the addition of purified metal chloride and a then adjusting the pH of the solution. For example, copper(II) complexes of glycyl-L-histidyl-L-lysine ("GHL") with a molar ratio of peptide to metal of 1:1, 2:1, or greater (e.g., 3:1), may be prepared by dissolving a given weight of GHL in distilled water (e.g., 50 mg/ml), and adding the desired molar amount of purified copper(II) chloride. The pH of the resulting peptide solution is then adjusted to about 7.0 by the addition of a sodium hydroxide solution. Similar metal:peptide complexes may be prepared with manganese(II) by substituting manganese(II) chloride for the copper(II) chloride in the procedure described above. Alternatively, metal salts other than the metal chloride may be utilized, such as copper(II) acetate or copper(II) sulfate.

EXAMPLE 2

Synthesis of Glycyl-L-Histidyl-L-Lysine Octyl Ester:Copper (II)

A mixture of $N^e$-benzyloxycarbonyl-L-Lysine, n-octanol, benzene, and p-toluenesulfonic acid monohydrate was refluxed overnight using a Dean-Stark trap to remove water. After cooling, dry ethyl ether was added. The solution was then allowed to precipitate at 0° C. overnight. A portion of the precipitate solid was added to 50 ml of potassium carbonate solution and 50 ml of dichloromethane. After extraction, the layers were separated and the organic phase was washed with water and brine, then dried with anhydrous magnesium sulfate. Filtration, evaporation and purification by flash column chromatography gave n-octyl $N^e$-benzyloxycarbonyl-L-lysinate.

The product was dissolved in tetrahydrofuran and mixed with $N^a$-t-butyloxycarbonyl-$N^{im}$-benzyloxycarbonyl-L-histidine, isobutyl chloroformate and N-methylmorpholine. After evaporation, water and ethyl acetate were added. The product was extracted into the organic phase, which was dried with anhydrous magnesium sulfate. Filtration, evaporation, and purification by flash column chromatography gave n-octyl $N^a$-t- butyloxycarbonyl-$N^{im}$-benzyloxycarbonyl-L-histidyl-$N^c$-benzyloxycarbonyl-L-lysinate.

The product was dissolved in 50% trifluoroacetic acid in dichloromethane for 30 minutes, then evaporated, forming n-octyl $N^{im}$-benzyloxycarbonyl-L-histidyl-$N^c$-benzyloxycarbonyl-L-lysinate. This was dissolved in tetrahydrofuran, and isobutyl chloroformates. N-methylmorpholine and benzyloxycarbonylglycine were added to form n-octyl benzyloxycarbonylglycyl-$N^{im}$-benzyloxycarbonyl-L-histidyl-$N^c$-benzyloxycarbonyl-L-lysinate. This was dissolved in glacial acetic acid and hydrogenated overnight in the presence of 10% Pd-C catalyst.

The resultant n-octyl ester of glycyl-L-histidyl-L-lysine was converted to the copper(II) complex by dissolving water and mixing with equimolar copper(II) acetate. The pH was raised to neutrality with sodium hydroxide. The solution was centrifuged at 20,000 C. g for 1 hour at 3° C. to remove poorly soluble material. The supernatant solution was lyophilized to obtain glycyl-L-histidyl-L-lysine n-octyl ester:copper(II).

EXAMPLE 3

Synthesis of Glycyl-L-Histidyl-L-lysine N-Stearyl Ester:Copper(II)

A mixture of $N^c$-benzyloxycarbonyl-L-lysine, n-stearyl alcohol, benzene, and p-toluenesulfonic acid monohydrate was refluxed overnight using a Dean-Stark trap to remove water. After cooling, dry propyl ether was added to increase the total volume sixfold. The product was allowed to precipitate at 0° C. overnight and filtered. A portion of the precipitate solid was added to 50 ml of potassium carbonate solution and 50 ml of dichloromethane. After extraction, the layers were separated and the organic phase was washed with water and brine, then dried with anhydrous magnesium sulfate. Filtration, evaporation and purification by flash column chromatography gave n-stearyl $N^c$-benzyloxycarbonyl-L-lysinate.

The product was dissolved in tetrahydrofuran and mixed with $N^a$-t-butyloxycarbonyl-$N^{im}$-benzyloxycarbonyl-L-histidine, isobutyl chloroformate and N-methylmorpholine. After evaporation, water and propyl acetate were added. The product was extracted into the organic phase, which was dried with anhydrous magnesium sulfate. Filtration, evaporation, and purification by flash column chromatography gave n-stearyl $N^a$-t-butyloxycarbonyl-$N^{im}$-benzyloxycarbonyl-L-histidyl-$N^c$-benzyloxycarbonyl-L-lysinate. This was dissolved in tetrahydrofuran, and isobutyl chloroformate, N-methylmorpholine and benzyloxycarbonylglycine were added to form n-stearyl benzyloxycarbonylglycyl-$N^{im}$-benzyloxycarbonyl-L-histidyl-$N^c$-benzyloxycarbonyl-L-lysinate. The product was dissolved in glacial acetic acid and hydrogenated overnight in the presence of 10% Pd-C catalyst.

The resultant n-stearyl ester of glycyl-L-histidyl-L-lysine was converted to the copper(II) complex by dissolving water and mixing with equimolar copper(II) acetate. The pH was raised to neutrality with sodium hydroxide. The solution was centrifuged at 20,000 X g for 1 hour at 3° C. to remove poorly soluble material. The supernatant solution was lyophilized to obtain glycyl-L-histidyl-L-lysine n-stearyl ester:copper(II).

By substituting n-palmityl alcohol (or any other alkyl alcohol) for the n-stearyl alcohol, glycyl-L-histidyl-L-lysine n-palmityl ester (or a corresponding alkyl ester) may be synthesized.

EXAMPLE 4

Synthesis of Glycyl-L-histidyl-L-lysine N-octylamide

A solution of $N^a$-t-butyloxycarbonyl-$N^c$-benzyloxycarbonyl-L-lysine in tetrahydrofuran was treated with N-methyl-morpholine, isobutyl chloroformate, and octylamine at −15° C. The resulting fully protected octyl amide was then treated with 50% trifluoroacetic acid in dichloromethane at room temperature, neutralized with saturated aqueous potassium bicarbonate solution, and extracted into ethyl acetate. Evaporation gave the deblocked lysinamide which was added to a solution prepared from $N^a$-t-butyloxycarbonyl-$N^{im}$-benzyloxycarbonyl-L-histidine, N-methylmorpholine, and isobutyl chloroformate in dry tetrahydrofuran at −15° C.

The fully protected dipeptide formed above was deblocked by treatment with 50% trifluoroacetic acid in dichloromethane at room temperature followed by neutralization with saturated aqueous potassium bicarbonate. Extraction into ethyl acetate and evaporation gave the partially deblocked dipeptide, which was added to a solution prepared from benzyloxycarbonyl glycine, N-methylmorpholine, and isobutyl chloroformate in dry tetrahydrofuran at −15° C. The resulting protected tripeptide was deblocked by treatment with hydrogen in the presence of 10% palladium on carbon in glacial acetic acid. Filtration and lyophilization gave glycyl-L-histidyl-L-lysine n-octyl amide as its triacetate salt.

EXAMPLE 5

Synthesis of Glycyl-L-histidyl-L-lysyl-L-valyl-L-phenylalanyl-L-valine

Multi-gram quantity of glycyl-L-histidyl-L-lysyl-L-valyl-L-phenylalanyl-L-valine was synthesized by standard solution phase method using t-butyloxycarbonyl protecting group for the alpha nitrogen, benzyloxycarbonyl group for side-chain protection and mixed anhydride method for coupling. Briefly stated, L-valine benzyl ester p-toluenesulfonate salt was coupled with t-butyloxycarbonyl-L-phenylalanine using isobutyl chloroformate and N-methylmorpholine as a coupling agent (2 hours at −20° C., then 1 hour at ambient temperature). The t-butyloxycarbonyl protecting group of the dipeptide was then removed by 30% trifluoroacetic acid in dichloromethane at room temperature for 30 minutes. Blocked amino acids (t-butyloxycarbonyl-L-valine, $N^a$-t-butyloxycarbonyl-$N^c$-benzyloxycarbonyl-L-lysine, $N^a$-t-butyloxycarbonyl-$N^{im}$-benzyloxycarbonyl-L-histidine, benzyloxycarbonylglycine) were added in sequential order, and t-butyloxycarbonyl protecting groups were removed to obtain the desired peptide. The final peptide was completely deprotected using hydrogen gas in acetic acid for 5 days in the presence of 10% Pd-C catalyst. The final peptide was lyophilized from water to obtain the tri-acetate salt.

EXAMPLE 6

Synthesis of L-alanyl-L-histidyl-L-lysine $N^c$-benzyloxycarbonyl-L-lysine benzyl ester hydrochloride salt was suspended in tetrahydrofuran (THF) and coupled with $N^a$-t-butyloxycarbonyl-$N^{im}$-benzyloxycarbonyl-L-histidine using isobutyl chloroformate and N-methylmorpholine (2 equivalents) in THF.

After two hours at −20° C. and an additional hour at ambient temperature, the reaction was quenched with 2N aqueous potassium bicarbonate. The product was extracted into ethyl acetate, washed with 1M aqueous citric acid, and saturated sodium bicarbonate. The organic phase was dried over anhydrous sodium sulfate. Filtration and evaporation gave benzyl $N^a$-t-butyloxycarbonyl-$N^{im}$-benzyloxycarbonyl-L-histidyl-$N^e$-benzyloxycarbonyl-L-lysinate.

The product was dissolved in 30% trifluoroacetic acid in dichloromethane for 30 minutes, then evaporate, forming benzyl $N^{im}$-benzyloxycarbonyl-L-histidyl-$N^e$-benzyloxycarbonyl-L-lysinate. This was dissolved in tetrahydrofuran, and isobutyl chloroformate, N-methyl-morpholine and benzyloxycarbonylalanine were added to form benzyl benzyloxycarbonylalanyl-$N^{im}$-benzyloxycarbonyl-L-histidyl-$N^e$-benzyloxycarbonyl-L-lysinate. This product was then dissolved in acetic acid and hydrogenated overnight in the presence of 10% Pd-C catalyst. The resultant alanyl-L-histidyl-L-lysine was lyophilized from water several times to yield the desired tripeptide as a diacetate salt.

EXAMPLE 7

Synthesis of L-lysyl-L-histidyl-glycine $N^a$-t-butyloxycarbonyl-$N^{im}$-benzyloxycarbonyl-L-histidine was dissolved in tetrahydrofuran (THF) and neutralized with one equivalent of N-methylmorpholine. It was then coupled with benzyl glycinate p-toluenesulfonate salt using isobutyl chloroformate and N-methylmorpholine. After two hours at −20° C. and an additional hour at ambient temperature, the reaction was quenched with 2N aqueous potassium bicarbonate. The product was extracted into ethyl acetate, washed with 1M aqueous citric acid, and saturated sodium bicarbonate. The organic phase was dried over anhydrous sodium sulfate. Filtration and evaporation gave benzyl $N^a$-t-butyloxycarbonyl-$N^{im}$-benzyloxycarbonyl-L-histidyl-glycinate.

This product was dissolved in anhydrous methanolic hydrogen chloride (saturated at 0° C.) for 5 minutes, followed by removal of solvent under reduced pressure, forming benzyl $N^{im}$-benzyloxycarbonyl-L-histidyl-glycinate. This was dissolved in tetrahydrofuran, and isobutyl chloroformate, N-methylmorpholine and $N^a,N^e$-dibenzyloxycarbonyl-L-lysine were added to form benzyl $N^a,N^e$-dibenzyloxycarbonyl-L-lysyl-$N^{im}$-benzyloxycarbonyl-L-histidyl-glycinate (3 hours at −20° C., the 1 hour at ambient temperature). This product was then dissolved in methanol/acetic acid, 1:1 (v/v), and hydrogenated overnight in the presence of 10% Pd-C catalyst. The resultant L-lysyl-L-histidyl-glycine was lyophilized from water several times, then purified by liquid chromatography on a C-18 reverse-phase column to yield the desired tripeptide triacetate salt as a foamy white solid.

EXAMPLE 8

Synthesis of L-lysyl-L-histidyl-glycine amide $N^a$-t-butyloxycarbonyl-$N^{im}$-benzyloxycarbonyl-L-histidine was dissolved in tetrahydrofuran (THF) and neutralized with one equivalent of N-methylmorpholine. It was then coupled with glycinamide hydrochloride using isobutyl chloroformate and N-methylmorpholine. After two hours at −20° C. and an additional hour at ambient temperature, the reaction was quenched with 2N aqueous potassium bicarbonate. This product was extracted into ethyl acetate, washed with 1M aqueous citric acid, and saturated sodium bicarbonate. The organic phase was dried over anhydrous sodium sulfate. Filtration and evaporation gave $N^a$-t-butyloxycarbonyl-$N^{im}$-benzyloxycarbonyl-L-histidyl-glycine amide.

The product was dissolved in anhydrous methanolic hydrogen chloride (saturated at 0° C.) for 30 minutes, followed by removal of solvent under reduced pressure, forming $N^{im}$-benzyloxycarbonyl-L-histidyl-glycine amide. This was dissolved in tetrahydrofuran, and isobutyl chloroformate, N-methylmorpholine and $N^a,N^e$-dibenzyloxycarbonyl-L-lysine were added to form benzyl $N^a,N^e$-dibenzyloxycarbonyl-L-lysyl-$N^{im}$-benzyloxycarbonyl-L-histidyl-glycine amide (3 hours at −20° C., then 1 hour at ambient temperature). This product was then dissolved in glacial acetic acid and hydrogenated overnight in the presence of 10% Pd-C catalyst. The resultant L-lysyl-L-histidyl-glycine amide was lyophilized from water several times, then purified by liquid chromatography on a C-18 reverse-phase column to yield the desired tripeptide amide as a triacetate salt.

EXAMPLE 9

Synthesis of L-lysyl-L-histidyl-glycine N-octyl Ester

Glycine, octyl alcohol, p-toluenesulfonic acid monohydrate, and benzene were refluxed together over a period of 24 hours using a Dean-Stark trap to azeotropically remove the evolved water. After cooling to room temperature and then adding dry ethyl ether, octyl glycinate p-toluenesulfonate was collected by suction filtration. The salt was treated with saturated sodium bicarbonate solution and extracted into dichloromethane. Evaporation gave the free amine, which was redissolved in dry tetrahydrofuran (THF) and added to a stirring solution of $N^a$-t-butyloxycarbonyl-$N^{im}$-benzyloxycarbonyl-L-histidine, N-methylmorpholine, and isobutyl chloroformate in dry THF at −20° C. and an additional hour at ambient temperature, the reaction was quenched with a 2N aqueous potassium bicarbonate. The product was extracted into ethyl acetate, washed with 1M citric acid, and saturated sodium bicarbonate. The organic phase was dried over anhydrous sodium sulfate, filtered and evaporated.

The resulting fully protected dipeptide ester was treated with 30% trifluoroacetic acid in dichloromethane at ambient temperature for 40 minutes, neutralized with saturated aqueous sodium bicarbonate solution, and extracted into ethyl acetate. Evaporation gave the partially deprotected dipeptide, which was redissolved in dry THF and added to a stirring solution of $N^a,N^e$-dibenzyloxycarbonyl-L-lysine, N-methylmorpholine an isobutyl chloroformate in dry THF at −20° C. The formed, fully protected tripeptide ester was totally deprotected by treatment with hydrogen gas in glacial acetic acid at ambient temperature in the presence of 10% Pd-C catalyst. Filtration through a layer of Celite, lyophilization from water, and purification by liquid chromatography on a C-18 reverse-phase column gave the desired tripeptide ester as its triacetate salt.

EXAMPLE 10

Synthesis of L-lysyl-L-histidyl-glycyl-L-valyl-L-phenylalanyl-L-valine

Multi-gram quantity of L-lysyl-L-histidyl-glycyl-L-valyl-L-phenylalanyl-L-valine was synthesized by standard solution phase method using t-butyloxycarbonyl protecting group for the alpha nitrogen, benzyloxycarbonyl group for side-chain protection and mixed anhydride method for coupling. Briefly stated, L-valine benzyl ester p-toluenesulfonate salt was coupled with t-butyloxycarbonyl-L-phenylalanine using isobutyl chloroformate and N-methylomorpholine as coupling agent (2 hours at −20° C., then 1 hour at ambient temperature). The t-butyloxycarbonyl protecting group of the dipeptide was then removed by 30% trifluoroacetic acid in dichloromethane at room temperature for 30 minutes. Blocked amino acids (t-butyloxycarbonyl-L-valine, t-butyloxycarbonylglycine, $N^a$-t-butyloxycarbonyl-$N^{im}$-benzyloxycarbonyl-L-histidine, $N^a$, $N^e$-dibenzyloxycarbonyl-L-lysine) were added in sequential order and t-butyloxycarbonyl protecting groups were removed to obtain the desired peptide. The final peptide was completely deprotected using hydrogen gas in glacial acetic acid for five days in the presence of 10% Pd-C catalyst. The final peptide was lyophilized from water and purified by liquid chromatography on a C-18 reverse phase column to produce the desired hexapeptide in multi-gram quantity.

The above systematic synthesis proved advantageous over some of the solid phase methods in providing multi-gram quantity of the desired peptide in high purity with minimal purification.

EXAMPLE 11

Synthesis of Glycyl-L-Histidyl-L-Caprolactam

L(−)-3-amino-e-caprolactam was dissolved in tetrahydrofuran (THF) then coupled with $N^a$-t-butyloxycarbonyl-$N^{im}$-benzyloxycarbonyl-L-histidine using isobutyl chloroformate and N-methylmorpholine in THF. After two hours at −20° C. and an additional hour at ambient temperature, the reaction was quenched with 2N aqueous potassium bicarbonate. This produre was extracted into ethyl acetate, washed with 1M aqueous citric acid, and saturated sodium bicarbonate. The organic phase was dried over anhydrous sodium sulfate. Filtration and evaporation gave $N^a$-t-butyloxycarbonyl-$N^{im}$-benxyloxycarbonyl-L-histidyl-L-caprolactam.

The above protected dipeptide was dissolved in 30% trifluoroacetic acid in dichloromethane for 30 minutes, then evaporated, forming $N^{im}$-benzyloxycarbonyl-L-histidyl-L-caprolactam. This was then dissolved in tetrahydrofuran, and isobutyl chloroformate, N-methylmorpholine and benzyloxycarbonylglycine were added to form benzyloxycarbonylglycyl-$N^{im}$-benzyloxycarbonyl-L-histidyl-L-caprolactam. This product was recrystallized once from ethyl acetate then dissolved in acetic acid and hydrogenated overnight in the presence of 10% Pd-C catalyst. The resultant glycyl-L-histidyl-L-caprolactam was lyophilized from water several times, then purified by liquid chromatography on a C-18 reverse-phase column to yield the desired tripeptide as a diacetate salt.

EXAMPLE 12

Synthesis of L-Histidyl-Glycyl-L-Lysine $N^e$-benxyloxycarbonyl-L-lysine benzyl ester hydrochloride salt was suspended in tetrahydrofuran (THF) and coupled with $N^a$-t-butyloxycarbonylglycine using isobutyl chloroformate and N-methylmorpholine in THF. After two hours at −20° C. and an additional hour at ambient temperature, the reaction was quenched with 2N aqueous potassium bicarbonate. The produce was extracted into ethyl acetate, washed with 1M aqueous citric acid, and saturated sodium bicarbonate. The organic phase was dried over anhydous sodium sulfate. Filtration and evaporation gave benzyl $N^a$-t-butyloxycarbonyl-glycyl-$N^e$-benzyloxycarbonyl-L-lysinate.

The product was dissolved in 30% trifluoroacetic acid in dichloromethane for 30 minutes, then evaporated, forming benzyl glycyl-$N^e$-benzyloxycarbonyl-L-lysinate. This was dissolved in tetrahydrofuran, and isobutyl chloroformate, N-methylmorpholine and $N^a$-benzyloxycarbonyl-$N^{im}$-benzyloxycarbonyl-L-histidine were added to form benzyl $N^a$-benzyloxycarbonyl-$N^{im}$-benzyloxycarbonyl-L-histidyl-glycyl-$N^e$-benzyloxycarbonyl-L-lysinate. This product was then dissolved in acetic acid and hydrogenated overnight in the presence of 10% Pd-C catalyst. The resultant L-histidyl-glycyl-L-lysine was lyophilized from water several times to yield the desired tripeptide as a diacetate salt.

EXAMPLE 13

Superoxide Dismutase Mimetic Activity of Hydrophobic Metal:Peptide Complexes

Metal:peptide complexes of the present invention which contain long chain aliphatic esters or other functional groups which alter the hydrophobic nature of the peptide possess unexpectedly high SOD activity when compared to glycyl-L-histidyl-L-lysine:copper(II) ("GHL-Cu"). Peptides which posses SOD activity are termed "SOD mimetics." In this example, superoxide dismutase mimetic activity was measured by the xanthine oxidase/NBT method (Oberley and Spitz, Handbook of Methods for Oxygen Radical Research, R. Greenwald ed., pp. 217-220, 1985; Auclair and Voisin, Handbook of Methods for Oxygen Radical Research, R. Greenwald ed., pp. 123-132, 1985). The reactions contained the following: 100 uM xanthine, 56 uM NBT (nitro blue tetrazolium) 1 unit of catalase, and 50 mM potassium phosphate buffer, pH 7.8. The reaction was initiated by the addition of xanthine oxidase in sufficient quantity to obtain an increase in absorbance at 560 nm of approximately 0.025/min. in a total sample volume of 1.7 ml. The xanthine oxidase was prepared fresh daily and stored on ice until used. All the components of the reaction are added except the xanthine oxidase and the spectrophotometer was adjusted to zero at 560 nm. The reaction was initiated by the addition of the xanthine oxidase. All reagents were obtained from Sigma Chemical Co.

Measurements of the absorbance at 560 nm were taken at 1-2 minute intervals for at least 16 minutes following addition of xanthine oxidase. A control consisted of reactions containing no metal:peptide complex.

One unit of SOD activity was taken as that amount of sample in micromoles which inhibits the control reaction with the NBT by 50%. The relative activity is obtained by comparing the micromoles of metal:peptide complex necessary to produce a 50% inhibition of the control reactions. The lower the value, the more active the compound is as a SOD mimetic. GHL-Cu is included in all experiments to serve as a positive control (i.e., a complex known to possess SOD mimetic activity). The inclusion of GHL-Cu permits comparison of all complexes tested relative to the activity exhibited by GHL-Cu. All complexes were tested at a 2:1 molar ratio of peptide to metal. The results of this experiment are summarized in Table 1. It should be noted that the absolute value found in enzymatic assays for SOD mimetic activity varries depending upon the enzyme lot used in the evaluation. Thus, the inclusion of GHL-Cu permits comparisons from experiment to experiment based on a normalized activity relative to GHL-Cu.

TABLE 1

EFFECT OF HYDROPHYLIC MODIFICATIONS ON SOD MIMETIC ACTIVITY

| COMPOUND | CONC. FOR 50% INHIB. (umoles/ml) | RELATIVE to GHL-Cu |
|---|---|---|
| A GHL:Cu | 0.059 | 100 |
| GHL-Octyl Ester:Cu | 0.007 | 810 |
| B GHL:Cu | 0.063 | 100 |
| GHLVFV:Cu | 0.023 | 229 |
| C GHL:Cu | 0.055 | 100 |
| GHLAFA:Cu | 0.010 | 561 |
| GHL-Palmityl Ester:Cu | 0.024 | 231 |
| D GHL:Cu | 0.006 | 100 |
| LHG-Octyl Ester:Cu | 0.010 | 60 |
| LHGVFV:Cu | 0.013 | 46 |
| E GHL:Cu | 0.031 | 100 |
| GHL-Octyl Amide:Cu | 0.017 | 182 |

NOTES TO TABLE 1:
GHL:Cu = glycyl-L-histidyl-L-lysine:copper(II)
GHL-Octyl Ester:Cu = glycyl-L-histidyl-L-lysine n-octyl ester:copper(II)
GHLVFV:Cu = glycyl-L-histidyl-L-lysyl-L-valyl-L-phenylalanyl-L-valine:copper(II)
GHLAFA:Cu = glycyl-L-histidyl-L-lysyl-L-alanyl-L-phenylalanyl-L-alanine:copper(II)
GHL-Palmityl Ester:Cu = glycyl-L-histidyl-L-lysine n-palmityl ester:copper(II)
LHG-Octyl Ester:Cu = lysyl-L-histidyl-L-glycine n-octyl ester:copper(II)
LHGVFV:Cu = lysyl-L-histidyl-glycyl-L-valyl-L-phenylalanyl-L-valine:copper(II)
GHL-Octyl Amide:Cu = glycyl-L-histidyl-L-lysine n-octyl amide:copper(II)

EXAMPLE 14

Superoxide Dismutase Mimetic Activity of Metal:Peptide Complexes

Metal:peptide complexes of the present invention containing modifications in the amino acid sequence or other modifications to individual amino acid components possess unexpectedly high SOD activity when compared to GHL-Cu.

In this example, superoxide dismutase was measured by the xanthine oxidase/NBT method as described in Example 13. Each complex was tested relative to GHL-Cu assayed at the same time. All complexes were tested at a 2:1 molar ratio of peptide to metal. The results of the this experiment are summarized in Table 2.

TABLE 2

EFFECT OF SEQUENCE AND AMINO ACID MODIFICATION ON SOD MIMETIC ACTIVITY

| COMPOUND | CONC. FOR 50% INHIB. (umoles/ml) | RELATIVE to GHL-Cu |
|---|---|---|
| A GHL:Cu | 0.047 | 100 |
| G(3-Benzyl)HL:Cu | 0.033 | 145 |
| G(3-Methyl)HL:Cu | 0.008 | 616 |
| B GHL:Cu | 0.020 | 100 |
| GHCadaverine:Cu | 0.017 | 118 |
| C GHL:Cu | 0.059 | 100 |
| G(3-Methyl)HLVFV:Cu | 0.017 | 231 |
| D GHL:Cu | 0.006 | 100 |
| GLH:Cu | 0.020 | 75 |
| LHG-Amide:Cu | 0.070 | 21 |
| E GHL:Cu | 0.031 | 100 |
| AHL:Cu | 0.006 | 563 |
| F GHL:Cu | 0.033 | 100 |
| GHCaprolactam:Cu | 0.0008 | 4500 |
| G GHL:Cu | 0.067 | 100 |

TABLE 2-continued

EFFECT OF SEQUENCE AND AMINO ACID MODIFICATION ON SOD MIMETIC ACTIVITY

| COMPOUND | CONC. FOR 50% INHIB. (umoles/ml) | RELATIVE to GHL-Cu |
|---|---|---|
| HGL:Cu | 0.0003 | 22300 |

NOTES TO TABLE 2:
GHL:Cu = glycyl-L-histidyl-L-lysine:copper(II)
G(3-Benzyl)HL:Cu = glycyl-L-(3-benzyl)-histidyl-L-lysine:copper(II)
G(3-Methyl)HL:Cu = glycyl-L-(3-methyl)-histidyl-L-lysine:copper(II)
GHCadaverine:Cu = glycyl-L-histidyl-cadaverine:copper(II)
G(3-Methyl)HLVFV:Cu = glycy-L-(3-methyl)-histidyl-L-lysyl-L-valyl-L-phenylalanyl-L-valine:copper(II)
GLH:Cu = glycyl-L-lysyl-L-histidine:copper(II)
LHG-Amide:Cu = lysyl-L-histidyl-L-glycine amide:copper(II)
AHL:Cu = alanyl-L-histidyl-L-lysine:copper(II)
GHCaprolactam:Cu = lysyl-L-histidyl-caprolactam:copper(II)
HGL:Cu = L-histidyl-glycyl-L-lysine:copper(II)

EXAMPLE 15

Superoxide Dismutase Mimetic Activity of Metal:Peptide Complexes

Substitution of other metal ions copper (II) in the metal:peptide complex gives complexes with high SOD activity when compared to GHL-Cu.

In this example, superoxide dismutase was measured by the xanthine oxidase/NBT method as described in Example 13. Each compound was tested relative to GHL-Cu assayed at the same time. All complexes were tested at a 2:1 molar ratio of peptide to metal. The results of the this experiment are summarized in Table 3.

TABLE 3

EFFECT OF METAL ION ON SOD MIMETIC ACTIVITY

| COMPOUND | RATIO | CONC. FOR 50% INHIB. (umoles/ml) | RELATIVE to GHL-Cu |
|---|---|---|---|
| A GHL:Cu | 2:1 | 0.013 | 100 |
| GHL:Mn | 2:1 | 0.004 | 275 |
| GHL-Octyl:Cu | 2:1 | 0.011 | 100 |
| GHL-Octyl:Mn | 2:1 | 0.002 | 611 |
| B GHL:Cu | 2:1 | 0.040 | 100 |
| GHL:Mn | 2:1 | 0.001 | 4000 |
| HGL:Mn | 2:1 | 0.002 | 2000 |
| GLH:Mn | 2:1 | 0.006 | 2000 |
| AHL:Mn | 2:1 | 0.006 | 667 |

NOTES TO TABLE 3:
GHL:Cu = glycyl-L-histidyl-L-lysine:copper(II)
GHL:Mn = glycyl-L-histidyl-L-lysine:manganese(II)
GHL-Octyl:Cu = glycyl-L-histidyl-L-lysine n-octyl ester:copper(II)
GHL-Octyl:Mn = glycyl-L-histidyl-L-lysine n-octyl ester:manganese(II)
HGL:Mn = L-histidyl-glycyl-L-lysine:manganese(II)
GLH:Mn = glycyl-L-lysyl-L-histidine:manganese(II)
AHL:Mn = alanyl-L-histidyl-L-lysine:manganese(II)

EXAMPLE 16

Superoxide Dismutase Mimetic Activity of Metal:Peptide Complexes

The metal:peptide complexes of the present invention may be modified with the addition of a chelating agent to the metal:peptide complex to yield a ternary metal:peptide:chelating agent complex with enhanced SOD mimetic activity when compared to GHL-Cu. As mentioned previously, to form such a ternary complex, the molar ratio of metal to peptide to chelating agent must be considered. For example, if the ratio of peptide to metal is 2:1, the addition of a chelating agent to the metal:peptide complex is difficult due to site occupancy by the peptide. However, by keeping the ratio of metal to peptide near 1:1 a chelating agent may be may be added.

In this example, superoxide dismutase was measured by the xanthine oxidase/NBT method as described in Example 13. Each compound was tested relative to GHL-Cu or glycyl-L-histidyl-L-lysyl-L-valyl-L-phenylalanyl-valine:copper(II) ("GHLVFV-Cu") assayed at the same time. In this example, the amount of complex for 50% inhibition is expressed as ug copper-(II) added per reaction necessary to achieve 50% inhibition of the control reaction. The results of this experiment are summarized in Table 4.

TABLE 4
EFFECT OF ADDITIONAL CHELATION GROUPS ON SOD MIMETIC ACTIVITY

| COMPOUND | RATIO | CONC. FOR 50% INHIB. (umoles/ml) | RELATIVE to GHL-Cu |
|---|---|---|---|
| A GHL:Cu | 2:1 | 3.2 | 100 |
| GHL:Cu:H | 1:1:1 | 0.2 | 1600 |
| GHL:Cu:Im | 1:1:1 | 1.3 | 246 |
| B GHLVFV:Cu | 2:1 | 2.8 | 100 |
| GHLVFV:Cu:H | 1:1:1 | 0.2 | 1400 |
| GHLVFV:Cu:Im | 1:1:1 | 0.3 | 930 |

NOTES TO TABLE 4.
GHL·Cu = glycyl-L-histidyl-L-lysine:copper(II)
GHL·Cu·H = glycyl-L-histidyl-L-lysine:copper(II):histidine
GHL·Cu·Im = glycyl-L-histidyl-L-lysine:copper(II):imidazole
GHLVFV·Cu = glycyl-L-histidyl-L-lysyl-L-valyl-L-phenylalanyl-L-valine:copper(II)
GHLVFV·Cu·H = glycyl-L-histidyl-L-lysyl-L-valyl-L-phenylalanyl-L-valine:copper(II):histidine
GHLVFV·Cu·Im = glycyl-L-histidyl-L-lysyl-L-valyl-L-phenylalanyl-L-valine:copper(II):imidazole

EXAMPLE 17

Superoxide Dismutase Mimetic Activity of Metal:Peptide Complexes Containing Albumin Binding Moieties Metal:peptide complexes of the present invention containing tryptophan demonstrate enhanced SOD mimetic activity relative to the GHL-Cu.

In this example, superoxide dismutase was measured by the xanthine oxidase/NBT method as described in Example 13. Each compound was tested relative to GHL-Cu assayed at the same time. The results of this experiment are summarized in Table 5.

TABLE 5
EFFECT ON SOD MIMETIC ACTIVITY BY ALBUMIN BINDING MOIETIES

| COMPOUND | RATIO | CONC. FOR 50% INHIB. (umoles/ml) | RELATIVE to GHL-Cu |
|---|---|---|---|
| A GHL:Cu | 2:1 | 0.059 | 100 |
| G(3-Methyl)HLGW:Cu | 2:1 | 0.011 | 521 |
| B GHL:Cu | 2:1 | 0.047 | 100 |
| GHLW:Cu | 2:1 | 0.001 | 4700 |

NOTES TO TABLE 5.
GHL:Cu = glycyl-L-histidyl-L-lysine:copper(II)
G(3-Methyl)HLGW:Cu = glycyl-L-(3-methyl)-histidyl-L-lysyl-glycyl-L-tryptophan:copper(II)
GHLW:Cu = glycyl-L-histidyl-L-lysyl-L-tryptophan:copper(II)

EXAMPLE 18

Inhibition of Ferritin Iron Release by Metal:Peptide Complexes

Iron metabolism is involved in lipid peroxidation. One of the mechanisms for this is the release of iron, Fe(III)/Fe(II), from ferritin, the major storage site of iron in the body, and subsequent participation of the free Fe(III)/Fe(II) in lipid peroxidation reactions. Iron release from ferritin is dependent on the generation of superoxide anion in the reactions. In an animal, superoxide anion is generated at the site of a wound or chronic inflammation by host defense mechanisms such as the neutrophils. The metal:peptide complexes of the present invention inhibit the release of Fe(III)/Fe(II) from ferritin.

Iron release from ferritin was measured by incubating ferritin with 10 um of a metal:peptide complexes of the present invention and determining the amount of iron released. Reaction mixtures contained 0.33 mM xanthine, 25 mU/ml xanthine oxidase, and 90 U/ml catalase as described in Example 13. In addition, 200 uM ferritin was added as a source of iron and 150 uM bathophenanthroline disulfonate to chelate and released iron. The release of iron was measured as an increase in the absorption of 535 nm due to the ironbathophenanthroline complex. The data is presented in Table 6 as this absorption rate and as a percent inhibition of a reaction with no additions. All the metal:peptide complexes are at a molar ratio of peptide to metal of 1:1.

TABLE 6
INHIBITION OF FERRITIN IRON RELEASE BY METAL:PEPTIDE COMPLEXES

| COMPOUND | RATE INC. $A_{535\,nm}$ min | PERCENT INHIBITION |
|---|---|---|
| NONE | 0.0060 | 0 |
| GHL:Cu | 0.0016 | 73% |
| GHL Octyl Ester:Cu | 0.0012 | 80% |
| GHLVFV:Cu | 0.0011 | 82% |
| G(3-Methyl)HL:Cu | 0.0010 | 83% |
| HGL:Cu | 0.0008 | 87% |

NOTES TO TABLE 6:
GHL:Cu = glycyl-L-histydyl-L-lysine:copper(II)
GHL Octyl Ester:Cu = glycyl-L-histidyl-L-lysine n-octyl ester:copper(II)
GHLVFV:Cu = glycyl-L-histidyl-L-lysyl-L-valyl-L-phenylalanyl-L-valine:copper(II)
G(3-Methyl)HL·Cu = glycyl-L-(3-methyl)-histidyl-L-lysine:copper(II)
HGL·Cu = L-histidyl-glycyl-L-lysine:copper(II)

EXAMPLE 19

Inhibition of Ferritin and Superoxide Anion Dependent Lipid Peroxidation by Metal:Peptide Complexes The iron released from ferritin can participate in lipid peroxidation reactions. Metal:peptide complexes of the present invention inhibit the lipid peroxidation mediated by the release of Fe(III)/Fe(II) from ferritin.

Lipid peroxidation was measured by determining the oxidation of lipids in liposomes prepared from rat liver lipids. Incubations were as described in Example 18 except that rat liver lipid microsomes were included. The oxidation was followed by determining the amount of malondialdehyde ("MDA") formed during the reaction. The data is presented in Table 7 as this absorption rate and as a percent inhibition of a reaction with no additions. All the metal:peptide complexes are at a molar ratio of peptide to metal of 1:1.

TABLE 7
INHIBITION OF SUPEROXIDE AND FERRITIN DEPENDENT LIPID PEROXIDATION BY METAL:PEPTIDE COMPLEXES

| COMPOUND | RATE nmole MDA/min/ml | PERCENT INHIBITION |
|---|---|---|
| A NONE | 0.220 | 0 |
| GHL:Cu | 0.084 | 62% |
| GHL Octyl Ester:Cu | 0.060 | 73% |

TABLE 7-continued

INHIBITION OF SUPEROXIDE AND FERRITIN DEPENDENT LIPID PEROXIDATION BY METAL:PEPTIDE COMPLEXES

| COMPOUND | RATE nmole MDA min/ml | PERCENT INHIBITION |
| --- | --- | --- |
| GHLVFV:Cu | 0.140 | 36% |
| B NONE | 0.150 | 0 |
| G(3-Methyl)HL:Cu | 0.104 | 31% |
| HGL:Cu | 0.020 | 87% |

NOTES TO TABLE 7:
GHL:Cu = glycyl-L-histidyl-L-lysine:copper(II)
GHL Octyl Ester:Cu = glycyl-L-histidyl-L-lysine n-octyl ester:copper(II)
GHLVFV:Cu = glycyl-L-histidyl-L-lysyl-L-valyl-L-phenylalanyl-L-valine:copper(II)
G(3-Methyl)HL:Cu = glycyl-L-(3-methyl)-histidyl-L-lysine:copper(II)
HGL:Cu = L-histidyl-glycyl-L-lysine:copper(II)

From the foregoing, it will be appreciated that, although specific embodiments of the invention have been described herein for purposes of illustration, various modifications may be made without deviating from the spirit and scope of the invention. Accordingly, the invention is not to be limited except as by the appended claims.

I claim:

1. A metal:peptide complex possessing anti-oxidative and anti-inflammatory activity, said complex having the general formula:

[glycyl-L-histidyl-L-lysine-R]:metal wherein

R is an aminoalkyl moiety containing from 1 to 18 carbon atoms, or is L-tryptophan, (glycyl)$_y$-L-tryptophan, where $y=1-4$, L-prolyl-X$_1$-L-phenylalanyl-X$_2$ or X$_1$-L-phenylalanyl-X$_2$, where X$_1$ and X$_2$ are selected from the group consisting of L-valine, L-alanine and glycine, and where X$_1$ and X$_2$ are not both L-valine, (X$_3$)$_n$-L-tryptophan, where X$_3$ is a —CH$_2$— or —CH(OH)— moiety and $n=4-20$, or -(X$_4$)$_n$, where X$_4$ is a naturally occurring carbohydrate selected from the group consisting of glucose, mannose, galactose, glucosamine and galactosamine and $n=1-5$; and metal is copper(II) or manganese(II).

2. A metal:peptide complex possessing anti-oxidative and anti-inflammatory activity, said complex having the general formula:

[glycyl-R$_1$-R$_2$-R$_3$]:metal wherein

R$_1$ is selected from the group consisting of L-histidyl, L-(3-W)-histidyl and L-(5-W)-histidyl, where W is an alkyl moiety containing from 1 to 12 carbons atoms or aryl moiety containing from 6-12 carbon atoms;

R$_2$ is —NHCH((CH$_2$)$_n$NH$_3$+)CO— where $n=5-10$;

R$_3$ is —NH$_2$, an aminoalkyl moiety containing from 1 to 18 carbon atoms, or is L-tryptophan, (glycyl)$_y$-L-tryptophan, where $y=1-4$, L-prolyl-X$_1$-L-phenylalanyl-X$_2$ or X$_1$-L-phenylalanyl-X$_2$, where X$_1$ and X$_2$ are selected from the group consisting of L-valine, L-alanine and glycine, and where X$_1$ and X$_2$ are not both L-valine, (X$_3$)$_n$-L-tryptophan, where X$_3$ is a —CH$_2$— or —CH(OH)— moiety and $n=4-20$, or -(X$_4$)$_n$, where X$_4$ is a naturally occurring carbohydrate selected from the group consisting of glucose, mannose, galactose, glucosamine and galactosamine and $n=1-5$; and metal is copper(II) or manganese(II).

3. A metal:peptide complex possessing anti-oxidative and anti-inflammatory activity, said complex having the general formula:

[glycyl-R$_1$-R$_2$-R$_3$]:metal wherein

R$_1$ is selected from the group consisting of L-(3-W)-histidyl and L-(5-W)-histidyl where W is an alkyl moiety containing from 1 to 12 carbons atoms or aryl moiety containing from 6-12 carbon atoms;

R$_2$ is L-lysyl;

R$_3$ is —NH$_2$, an aminoalkyl moiety containing from 1 to 18 carbon atoms, or is L-tryptophan, (glycyl)$_y$-L-tryptophan, where $y=1-4$, L-prolyl-X$_1$-phenylalanyl-X$_2$ or X$_1$-L-phenylalanyl-X$_2$, where X$_1$ and X$_2$ are selected from the group consisting of L-valine, L-alanine and glycine, and where X$_1$ and X$_2$ are not both L-valine, (X$_3$)$_n$-L-tryptophan, where X$_3$ is a —CH$_2$— or —CH(OH)— moiety and $n=4-20$, or -(X$_4$)$_n$, where X$_4$ is a naturally occurring carbohydrate selected from the group consisting of glucose, mannose, galactose, glucosamine and galactosamine and $n=1-5$; and metal is copper(II) or manganese(II).

4. A metal:peptide complex possessing anti-oxidative and anti-inflammatory activity, said complex having the general formula:

[glycyl-R$_1$-R$_2$-R$_3$]:metal wherein

R$_1$ is selected from the group consisting of L-histidyl, L-(3-W)-histidyl and L-(5-W)-histidyl where W is an alkyl moiety containing from 1 to 12 carbons atoms or aryl moiety containing from 6-12 carbon atoms;

R$_2$ is a basic amino acid, a basic amino moiety, or a modified basic amino acid;

R$_3$ is hydrogen, —NH$_2$, an alkyl moiety containing from 1 to 18 carbon atoms, an aryl moiety containing from 6 to 12 carbon atoms, an alkoxy moiety containing from 1 to 18 carbon atoms, an aryloxy moiety containing from 6-12 carbon atoms, an aminoalkyl moiety containing from 1 to 18 carbon atoms, or is L-tryptophan, (glycyl)$_y$-L-tryptophan, where $y=1-4$, L-prolyl-X$_1$-L-phenylalanyl-X$_2$ or X$_1$-L-phenylalanyl-X$_2$, where X$_1$ and X$_2$ are selected from the group consisting of L-valine, L-alanine and glycine, (X$_3$)$_n$-tryptophan, where X$_3$ is a —CH$_2$— or —CH(OH)— moiety and $n=4-20$, or -(X$_4$)$_n$, where X$_4$ is a naturally occurring carbohydrate selected from the group consisting of glucose, mannose, galactose, glucosamine and galactosamine and $n=1-5$; and metal is copper(II) or manganese(II).

5. A metal:peptide complex possessing anti-oxidative and anti-inflammatory activity, said complex having the general formula:

[R$_1$-R$_2$-glycine-R$_3$]:metal wherein

R$_1$ is L-lysyl or —NHCH((CH$_2$)$_n$NH$_3$+)CO— where $n=5-10$;

$R_2$ is selected from the group consisting of L-histidyl, L-(3-W)-histidyl and L-(5-W)-histidyl where W is an alkyl moiety containing from 1 to 12 carbons atoms or aryl moiety containing from 6-12 carbon atoms;

$R_3$ is hydrogen, $-NH_2$, an alkyl moiety containing from 1 to 18 carbon atoms, an aryl moiety containing from 6 to 12 carbon atoms, an alkoxy moiety containing from 1 to 18 carbon atoms, an aryloxy moiety containing from 6-12 carbon atoms, an aminoalkyl moiety containing from 1 to 18 carbon atoms, or is L-tryptophan, (glycyl)$_y$-L-tryptophan, where y=1-4, L-prolyl-$X_1$-L-phenylalanyl-$X_2$ or $X_1$-L-phenylalanyl-$X_2$, where $X_1$ and $X_2$ are selected from the group consisting of L-valine, L-alanine and glycine, $(X_3)_n$-L-tryptophan, where $X_3$ is a $-CH_2-$ or $-CH(OH)-$ moiety and n=4-20, or $-(X_4)_n$, where $X_4$ is a naturally occurring carbohydrate selected from the group consisting of glucose, mannose, galactose, glucosamine and galactosamine and n=1-5; and metal is copper(II) or manganese(II).

6. A metal:peptide complex possessing anti-oxidative and anti-inflammatory activity, said complex having the general formula:

[$R_1$-$R_2$-$R_3$-$R_4$]:metal wherein $R_1$ is L-lysyl or $-NHCH((CH_2)_nNH_3^+)CO-$ where n=5-10;

$R_2$ is selected from the group consisting of L-histidyl, L-(3-W)-histidyl and L-(5-W)-histidyl where W is an alkyl moiety containing from 1 to 12 carbons atoms or aryl moiety containing from 6-12 carbon atoms;

$R_3$ is a basic amino acid, a basic amino moiety, or a modified basic amino acid;

$R_4$ is hydrogen, $-NH_2$, an alkyl moiety containing from 1 to 18 carbon atoms, an aryl moiety containing from 6 to 12 carbon atoms, an alkoxy moiety containing from 1 to 18 carbon atoms, an aryloxy moiety containing from 6-12 carbon atoms, an aminoalkyl moiety containing from 1 to 18 carbon atoms, or is L-tryptophan, (glycyl)$_y$-L-tryptophan, where y=1-4, L-prolyl-$X_1$-L-phenylalanyl-$X_2$ or $X_1$-L-phenylalanyl-$X_2$, where $X_1$ and $X_2$ are selected from the group consisting of L-valine, L-alanine and glycine, $(X_3)_n$-L-tryptophan, where $X_3$ is a $-CH_2-$ or $-CH(OH)-$ moiety and n=4-20, or $-(X_4)_n$, where $X_4$ is a naturally occurring carbohydrate selected from the group consisting of glucose, mannose, galactose, glucosamine and galactosamine and n=1-5; and metal is copper(II) or manganese(II).

7. A metal:peptide complex possessing anti-oxidative and anti-inflammatory activity, said complex having the general formula:

[$R_1$-glycyl-$R_2$-$R_3$]:metal wherein $R_1$ is selected from the group consisting of L-histidyl, L-(3-W)-histidyl and L-(5-W)-histidyl where W is an alkyl moiety containing from 1 to 12 carbons atoms or aryl moiety containing from 6-12 carbon atoms;

$R_2$ is L-lysyl, $-NHCH((CH_2)_nNH_3^+)CO-$, where n=5-10, or a basic amino acid, a basic amino moiety, or a modified basic amino acid;

$R_3$ is hydrogen, $-NH_2$, an alkyl moiety containing from 1 to 18 carbon atoms, an aryl moiety containing from 6 to 12 carbon atoms, an alkoxy moiety containing from 1 to 18 carbon atoms, an aryloxy moiety containing from 6-12 carbon atoms, an aminoalkyl moiety containing from 1 to 18 carbon atoms, or is L-tryptophan, (glycyl)$_y$-L-tryptophan, where y=1-4, L-prolyl-$X_1$-L-phenylalanyl-$X_2$ or $X_1$-L-phenylalanyl-$X_2$, where $X_1$ and $X_2$ are selected from the group consisting if L-valine, L-alanine and glycine, $(X_3)_n$-L-tryptophan, where $X_3$ is a $-CH_2-$ or $-CH(OH)-$ moiety and n=4-20, or $-(X_4)_n$, where $X_4$ is a naturally occurring carbohydrate selected from the group consisting of glucose, mannose, galactose, glucosamine and galactosamine and n=1-5; and metal is copper(II) or manganese(II).

8. A metal:peptide complex possessing anti-oxidative and anti-inflammatory activity, said complex having the general formula:

[L-alanyl-$R_1$-$R_2$-$R_3$]:metal wherein $R_1$ is selected from the group consisting of L-histidyl, L-(3-W)-histidyl and L-(5-W)-histidyl where W is an alkyl moiety containing from 1 to 12 carbons atoms or aryl moiety containing from 6-12 carbon atoms;

$R_2$ is L-lysyl or $-NHCH((CH_2)_nNH_3^+)CO-$, where n=5-10;

$R_3$ is $-NH_2$, an aminoalkyl moiety containing from 1 to 18 carbon atoms, or is L-tryptophan, (glycyl)$_y$-L-tryptophan, where y=1-4, L-prolyl-$X_1$-L-phenylalanyl-$X_2$ or $X_1$-L-phenylalanyl-$X_2$, where $X_1$ and $X_2$ are selected from the group consisting of L-valine, L-alanine and glycine, and where $X_1$ and $X_2$ are not both L-valine, $(X_3)_n$-L-tryptophan, where $X_3$ is a $-CH_2-$ or $-CH(OH)-$ moiety and n=4-20, or $-(X_4)_n$, where $X_4$ is a naturally occurring carbohydrate selected from the group consisting of glucose, mannose, galactose, glucosamine and galactosamine and n=1-5; and metal is copper(II) or manganese(II).

9. A metal:peptide complex possessing anti-oxidative and anti-inflammatory activity, said complex having the general formula:

[glycyl-$R_1$-$R_2$-$R_3$]:metal wherein $R_1$ is L-lysyl or $-NHCH((CH_2)_nNH_3^+)CO-$ where n=5-10

$R_2$ is selected from the group consisting of L-histidyl, L-(3-W)-histidyl and L-(5-W)-histidyl where W is an alkyl moiety containing from 1 to 12 carbons atoms or aryl moiety containing from 6-12 carbon atoms;

$R_3$ is hydrogen, $-NH_2$, an alkyl moiety containing from 1 to 18 carbon atoms, an aryl moiety containing from 6 to 12 carbon atoms, an alkoxy moiety containing from 1 to 18 carbon atoms, an aryloxy moiety containing from 6-12 carbon atoms, an aminoalkyl moiety containing from 1 to 18 carbon atoms, or is L-tryptophan, (glycyl)$_y$-L-tryptophan, where y=1-4, L-prolyl-$X_1$-L-phenylalanyl-$X_2$ or $X_1$-L-phenylalanyl-$X_2$, where $X_1$ and $X_2$ are selected from the group consisting of L-valine, L-alanine and glycine, $(X_3)_n$-L-tryptophan, where $X_3$ is a —$CH_2$— or —CH(OH)— moiety and n=4-20, or -$(X_4)_n$, where $X_4$ is a naturally occurring carbohydrate selected from the group consisting of glucose, mannose, galactose, glucosamine and galactosamine and n=1-5; and metal is copper(II) or manganese(II).

10. The metal:peptide complex of any one of claims 1-9, wherein the ratio of peptide to metal is 2:1.

11. The metal:peptide complex of any one of claims 1-9, further including a pharmaceutically acceptable carrier or diluent.

12. The metal:peptide complex of any one of claims 1-9, further including a chelating agent such that a ternary metal:peptide:chelating agent complex is formed, the chelating agent being imidazole or an imidazole-containing compound.

13. The metal:peptide complex of claim 12 wherein the imidazole-containing compound is histidine.

14. The metal:peptide complex of any one of claims 1-9, further including a chelating agent such that a ternary metal:peptide:chelating agent complex is formed, the chelating agent being cysteine or methionine.

15. A method for enhancing or restoring the resistance of a warm blooded animal to oxidative or inflammatory damage caused by release of reactive oxygen species by administering to the animal a therapeutically effective amount of a metal:peptide complex, said complex having the general formula:

[glycyl-L-histidyl-L-lysine-R]:metal wherein

R is an aminoalkyl moiety containing from 1 to 18 carbon atoms, or is L-tryptophan, (glycyl)$_y$-L-tryptophan, where y=1-4, L-prolyl-$X_1$-L-phenylalanyl-$X_2$ or $X_1$-L-phenylalanyl-$X_2$, where $X_1$ and $X_2$ are selected from the group consisting of L-valine, L-alanine and glycine, and where $X_1$ and $X_2$ are not both L-valine, $(X_3)_n$-L-tryptophan, where $X_3$ is a —$CH_2$— or —CH(OH)— moiety and n=4-20, or -$(X_4)_n$, where $X_4$ is a naturally occurring carbohydrate selected from the group consisting of glucose, mannose, galactose, glucosamine and galactosamine and n=1-5; and metal is copper(II) or manganese(II).

16. A method for enhancing or restoring the resistance of a warm blooded animal to oxidative or inflammatory damage caused by release of reactive oxygen species by administering to the animal a therapeutically effective amount of a metal:peptide complex, said complex having the general formula:

[glycyl-$R_1$-$R_2$-$R_3$]:metal wherein $R_1$ is selected from the group consisting of L-histidyl, L-(3-W)-histidyl and L-(5-W)-histidyl, where W is an alkyl moiety containing from 1 to 12 carbons atoms or aryl moiety containing from 6-12 carbon atoms;

$R_2$ is —NHCH(($CH_2)_n$$NH_3$+)CO— where n=5-10;

$R_3$ is —$NH_2$, an aminoalkyl moiety containing from 1 to 18 carbon atoms, or is L-tryptophan, (glycyl)$_y$-L-tryptophan, where y=1-4, L-prolyl-$X_1$-L-phenylalanyl-$X_2$ or $X_1$-L-phenylalanyl-$X_2$, where $X_1$ and $X_2$ are selected from the group consisting of L-valine, L-alanine and glycine, and where $X_1$ and $X_2$ are not both L-valine, $(X_3)_n$-L-tryptophan, where $X_3$ is a —$CH_2$— or —CH(OH)— moiety and n=4-20, or -$(X_4)_n$, where $X_4$ is a naturally occurring carbohydrate selected from the group consisting of glucose, mannose, galactose, glucosamine and galactosamine and n=1-5; and metal is copper(II) or manganese(II).

17. A method for enhancing or restoring the resistance of a warm blooded animal to oxidative or inflammatory damage caused by release of reactive oxygen species by administering to the animal a therapeutically effective amount of a metal:peptide complex, said complex having the general formula:

[glycyl-$R_1$-$R_2$-$R_3$]:metal wherein $R_1$ is selected from the group consisting of L-(3-W)-histidyl and L-(5-W)-histidyl where W is an alkyl moiety containing from 1 to 12 carbon atoms or aryl moiety containing from 6-12 carbon atoms;

$R_2$ is L-lysyl;

$R_3$ is —$NH_2$, an aminoalkyl moiety containing from 1 to 18 carbon atoms, or is L-tryptophan, (glycyl)$_y$-L-tryptophan, where y=1-4, L-prolyl-$X_1$-L-phenylalanyl-$X_2$ or $X_1$-L-phenylalanyl-$X_2$, where $X_1$ and $X_2$ are selected from the group consisting of L-valine, L-alanine and glycine, and where $X_1$ and $X_2$ are not both L-valine, $(X_3)_n$-L-tryptophan, where $X_3$ is a —$CH_2$— or —CH(OH)— moiety and n=4-20, or —$(X_4)_n$, where $X_4$ is a naturally occuring carbohydrate selected from the group consisting of glucose, mannose, galactose, glucosamine and galactosamine and n=1-5; and metal is copper(II) or manganese(II).

18. A method for enhancing or restoring the resistance of a warm blooded animal to oxidative or inflammatory damage caused by release of reactive oxygen species by administering to the animal a therapeutically effective amount of a metal:peptide complex, said complex having the general formula:

[glycyl-$R_1$-$R_2$-$R_3$]:metal wherein $R_1$ is selected from the group consisting of L-histidyl, L-(3-W)-histidyl and L-(5-W)-histidyl where W is an alkyl moiety containing from 1 to 12 carbons atoms or aryl moiety containing from 6-12 carbon atoms;

$R_2$ is a basic amino acid, a basic amino moiety, or a modified basic amino acid;

$R_3$ is hydrogen, —$NH_2$, an alkyl moiety containing from 1 to 18 carbon atoms, an aryl moiety containing from 6 to 12 carbon atoms, an alkoxy moiety containing from 1 to 18 carbon atoms, an aryloxy moiety containing from 6-12 carbon atoms, an aminoalkyl moiety containing from 1 to 18 carbon atoms, or is L-tryptophan, (glycyl)$_y$-L-tryptophan, where y=1-4, L-prolyl-$X_1$-L-phenylalanyl-$X_2$ or $X_1$-L-phenylalanyl-$X_2$, where $X_1$ and $X_2$ are selected from the group consisting of L-valine, L-alanine and glycine, $(X_3)_n$-L-tryptophan, where $X_3$ is a —$CH_2$— or —CH(OH)— moiety and n=4-20, or -$(X_4)_n$, where $X_4$ is a naturally occurring carbohydrate selected from the group consisting of glucose, mannose, galactose, glucosamine and galactosamine and n=1-5; and metal is copper(II) or manganese(II).

19. A method for enhancing or restoring the resistance of a warm blooded animal to oxidative or inflammatory damage caused by release of reactive oxygen species by administering to the animal a therapeutically effective amount of a metal:peptide complex, said complex having the general formula:

[$R_1$-$R_2$-glycine-$R_3$]:metal wherein $R_1$ is L-lysyl or —NHCH$((CH_2)_n$NH$_3^+$)CO— where n=5-10;

$R_2$ is selected from the group consisting of L-histidyl, L-(3-W)-histidyl and L-(5-W)-histidyl where W is an alkyl moiety containing from 1 to 12 carbons atoms or aryl moiety containing from 6-12 carbon atoms;

$R_3$ is hydrogen, —NH$_2$, an alkyl moiety containing from 1 to 18 carbon atoms, an aryl moiety containing from 6 to 12 carbon atoms, an alkoxy moiety containing from 1 to 18 carbon atoms, an aryloxy moiety containing from 6-12 carbon atoms, an aminoalkyl moiety containing from 1 to 18 carbon atoms, or is L-tryptophan, (glycyl)$_y$-L-tryptophan, where y=1-4, L-prolyl-$X_1$-L-phenylalanyl-$X_2$ or $X_1$-L-phenylalanyl-$X_2$, where $X_1$ and $X_2$ are selected from the group consisting of L-valine, L-alanine and glycine, $(X_3)_n$-L-tryptophan, where $X_3$ is a —CH$_2$— or —CH(OH)— moiety and n=4-20, or -$(X_4)_n$, where $X_4$ is a naturally occurring carbohydrate selected from the group consisting of glucose, mannose, galactose, glucosamine and galactosamine and n=1-5; and metal is copper(II) or manganese(II).

20. A method for enhancing or restoring the resistance of a warm blooded animal to oxidative or inflammatory damage caused by release of reactive oxygen species by administering to the animal a therapeutically effective amount of a metal:peptide complex, said complex having the general formula:

[$R_1$-$R_2$-$R_3$-$R_4$]:metal wherein $R_1$ is L-lysyl or —NHCH$((CH_2)_n$NH$_3^+$)CO— where n=5-10;

$R_2$ is selected from the group consisting of L-histidyl, L-(3-W)-histidyl and L-(5-W)-histidyl where W is an alkyl moiety containing from 1 to 12 carbons atoms or aryl moiety containing from 6-12 carbon atoms;

$R_3$ is a basic amino acid, a basic amino moiety, or a modified basic amino acid;

$R_4$ is hydrogen, —NH$_2$, an alkyl moiety containing from 1 to 18 carbon atoms, an aryl moiety containing from 6 to 12 carbon atoms, an alkoxy moiety containing from 1 to 18 carbon atoms, an aryloxy moiety containing from 6-12 carbon atoms, an aminoalkyl moiety containing from 1 to 18 carbon atoms, or is L-tryptophan, (gylcyl)$_y$-L-tryptophan, where y=1-4, L-prolyl-$X_1$-L-phenylalanyl-$X_2$ or $X_1$-L-phenylalanyl-$X_2$, where $X_1$ and $X_2$ are selected from the group consisting of L-valine, L-alanine and glycine, $(X_3)_n$-L-tryptophan, where $X_3$ is a —CH$_2$— or —CH(OH)— moiety and n=4-20, or -$(X_4)_n$, where $X_4$ is a naturally occurring carbohydrate selected from the group consisting of glucose, mannose, galactose, glucosamine and galactosamine and n=1-5; and metal is copper (II) or manganese (II).

21. A method for enhancing or restoring the resistance of a warm blooded animal to oxidative or inflammatory damage caused by release of reactive oxygen species by administering to the animal a therapeutically effective amount of a metal:peptide complex, said complex having the general formula:

[$R_1$-glycyl-$R_2$-$R_3$]:metal wherein $R_1$ is selected from the group consisting of L-histidyl, L-(3-W)-histidyl and L-(5-W)-histidyl where W is an alkyl moiety containing from 1 to 12 carbon atoms or aryl moiety containing from 6-12 carbon atoms;

$R_2$ is L-lysyl, —NHCH$((CH_2)_n$NH$_3^+$)CO—, where n=5-10, or a basic amino acid, a basic amino moiety, or a modified basic amino acid;

$R_3$ is hydrogen, —NH$_2$, an alkyl moiety containing from 1 to 18 carbon atoms, an aryl moiety containing from 6 to 12 carbon atoms, an alkoxy moiety containing from 1 to 18 carbon atoms, an aryloxy moiety containing from 6-12 carbon atoms, an aminoalkyl moiety containing from 1 to 18 carbon atoms, or is L-tryptophan, (glycyl)$_y$-L-tryptophan, where y=1-4, L-prolyl-$X_1$-L-phenylalanyl-$X_2$ or $X_1$-L-phenylalanyl-$X_2$, where $X_1$ and $X_2$ are selected from the group consisting of L-valine, L-alanine and glycine, $(X_3)_n$-L-tryptophan, where $X_3$ is a —CH$_2$— or —CH(OH)— moiety and n=4-20, or -$(X_4)_n$, where $X_4$ is a naturally occurring carbohydrate selected form the group consisting of glucose, mannose, galactose, glucosamine and galactosamine and n=1-5; and metal is copper(II) or manganese(II).

22. A method for enhancing or restoring the resistance of a warm blooded animal to oxidative or inflammatory damage caused by release of reactive oxygen species by administering to the animal a therapeutically effective amount of a metal:peptide complex, said complex having the general formula:

[L-alanyl-$R_1$-$R_2$-$R_3$]:metal wherein $R_1$ is selected from the group consisting of L-histidyl, L-(3-W)-histidyl and L-(5-W)-histidyl where W is an alkyl moiety containing from 1 to 12 carbons atoms or aryl moiety containing from 6-12 carbon atoms;

$R_2$ is L-lysyl or —NHCH$((CH_2)_n$NH$_3^+$)CO— where n=5-10;

$R_3$ is —NH$_2$, an aminoalkyl moiety containing from 1 to 18 carbon atoms, or is L-tryptophan, (glycyl)$_y$-L-tryptophan, where y=1-4, L-prolyl-$X_1$-L-phenylalanyl-$X_2$ or $X_1$-L-phenylalanyl-$X_2$, where $X_1$ and $X_2$ are selected from the group consisting of L-valine, L-alanine and glycine, and where $X_1$ and $X_2$ are not both L-valine, $(X_3)_n$-L-tryptophan, where $X_3$ is a —CH$_2$— or —CH(OH)— moiety and n=4-20, or -$(X_4)_n$, where $X_4$ is a naturally occurring carbohydrate selected from the group consisting of glucose, mannose, galactose, glucosamine and galactosamine and n=1-5; and metal is copper(II) or manganese(II).

23. A method for enhancing or restoring the resistance of a warm blooded animal to oxidative or inflammatory damage caused by release of reactive oxygen species by administering to the animal a therapeutically effective amount of a metal:peptide complex, said complex having the general formula:

[glycyl-$R_1$-$R_2$-$R_3$]:metal wherein $R_1$ is L-lysyl or —NHCH(($CH_2$)$_n$$NH_3^-$)CO— where n=5-10

$R_2$ is selected from the group consisting of L-histidyl, L-(3-W)-histidyl and L-(5-W)-histidyl where W is an alkyl moiety containing from 1 to 12 carbons atoms or aryl moiety containing from 6-12 carbon atoms;

$R_3$ is hydrogen, —$NH_2$, an alkyl moiety containing from 1 to 18 carbon atoms, an aryl moiety containing from 6 to 12 carbon atoms, an alkoxy moiety containing from 1 to 18 carbon atoms, an aryloxy moiety containing from 6-12 carbon atoms, an aminoalkyl moiety containing from 1 to 18 carbon atoms, or is L-tryptophan, (glycyl)$_y$-L-tryptophan, where y=1-4, L-prolyl-$X_1$-L-phenylalanyl-$X_2$ or $X_1$-L-phenylalanyl-$X_2$, where $X_1$ and $X_2$ are selected from the group consisting of L-valine, L-alanine and glycine, ($X_3$)$_n$-L-typtophan, where $X_3$ is a —$CH_2$— or —CH(OH)— moiety and n=4-20, or -($X_4$)$_n$, where $X_4$ is a naturally occurring carbohydrate selected from the group consisting of glucose, mannose, galactose, glucosamine and galactosamine and n=1-5; and metal is copper(II) or manganese(II).

24. The metal:peptide complex of any one of claims 15-23, wherein the peptide to metal ratio is 2:1.

25. The metal:peptide complex of any one of claims 15-23, further including a pharmaceutically acceptable carrier or diluent.

26. The metal:peptide complex of any one of claims 15-23, further including a chelating agent such that a ternary metal:peptide:chelating agent complex is formed, the chelating agent being imidazole or an imidazole-containing compound.

27. The metal:peptide complex of claim 26 wherein the imidazole-containing compound is histidine.

28. The metal:peptide complex of any one of claims 15-23, further including a chelating agent such that a ternary metal:peptide:chelating agent complex is formed, the chelating agent being cysteine or methionine.

29. A metal:peptide complex possessing anti-oxidative and anti-inflammatory activity, said complex having the formula:

[L-histidyl-glycyl-L-lysine]:copper(II).

30. The metal:peptide complex of claim 29, wherein the ratio of peptide to metal is 2:1.

31. The metal:peptide complex of claim 29, further including a pharmaceutically acceptable carrier or diluent.

32. The metal:peptide complex of claim 29, further including a chelating agent such that a ternary metal:peptide:chelating agent complex is formed, the chelating agent being imidazole or an imidazole-containing compound.

33. The metal:peptide complex of claim 32 wherein the imidazole-containing compound is histidine.

34. The metal:peptide complex of claim 29, further including a chelating agent such that a ternary metal:peptide:chelating agent complex is formed, the chelating agent being cysteine or methionine.

35. A method for enhancing or restoring the resistance of a warm-blooded animal to oxidative or inflammatory damage caused by release of reactive oxygen species by administering to the animal a therapeutically effective amount of a metal:peptide complex, said complex having the formula:

[L-histidyl-glycyl-L-lysine]:copper(II).

36. The method of claim 35, wherein the peptide to metal ratio of the metal:peptide complex is 2:1.

37. The method of claim 35, wherein the metal:peptide complex further includes a pharmaceutically acceptable carrier or diluent.

38. The method of claim 35, wherein the metal:peptide complex further includes a chelating agent such that a ternary metal:peptide:chelating agent complex is formed, the chelating agent being imidazole or an imidazole-containing compound.

39. The method of claim 38, wherein the imidazole-containing compound is histidine.

40. The method of claim 35, wherein the metal:peptide complex further includes a chelating agent such that a ternary metal:peptide:chelating agent complex is formed, the chelating agent being cysteine or methionine.

* * * * *

UNITED STATES PATENT AND TRADEMARK OFFICE
CERTIFICATE OF CORRECTION

PATENT NO. : 5,118,665
DATED : June 2, 1992
INVENTOR(S) : Loren R. Pickart

It is certified that error appears in the above-identified patent and that said Letters Patent is hereby corrected as shown below:

In column 22, claim 3, lines 18 and 19, please delete "L-prolyl-$X_1$-phenylalanyl-$X_2$ and substitute therefor -- L-prolyl-$X_1$-L-phenylalanyl-$X_2$ --.

In column 22, claim 4, line 53, please delete "$(X_3)_n$-tryptophan" and substitute therefor -- $(X_3)_n$-L-tryptophan --.

In column 23, claim 6, line 31, please delete "-NHCH((CH$_2$)$_n$NH$_3$-)CO-" and substitute therefor -- -NHCH((CH$_2$)$_n$NH$_3$+)CO- --.

In column 24, claim 7, line 1, please delete "-NHCH((CH$_2$)$_n$NH$_3$-)CO-" and substitute therefor -- -NHCH((CH$_2$)$_n$NH$_3$+)CO- --.

In column 27, claim 19, line 30, please delete "L-prolyl-$X_1$L-phenylalanyl-$X_2$" and substitute therefor -- L-prolyl-$X_1$-L-phenylalanyl-$X_2$ --.

Signed and Sealed this

Seventh Day of September, 1993

*Attest:*

BRUCE LEHMAN

*Attesting Officer*    *Commissioner of Patents and Trademarks*